US010253064B2

(12) United States Patent
Kuroda et al.

(10) Patent No.: US 10,253,064 B2
(45) Date of Patent: Apr. 9, 2019

(54) PURIFICATION METHOD, PURIFICATION KIT, AND SILICON OXIDE-BINDING TAG FOR USE THEREIN

(71) Applicant: Hiroshima University, Hiroshima (JP)

(72) Inventors: Akio Kuroda, Hiroshima (JP); Takeshi Ikeda, Hiroshima (JP); Hisakage Funabashi, Hiroshima (JP)

(73) Assignee: Hiroshima University, Hiroshima (JP)

( * ) Notice: Subject to any disclaimer, the term of this patent is extended or adjusted under 35 U.S.C. 154(b) by 92 days.

(21) Appl. No.: 15/521,256

(22) PCT Filed: Oct. 21, 2015

(86) PCT No.: PCT/JP2015/079753
§ 371 (c)(1),
(2) Date: Apr. 21, 2017

(87) PCT Pub. No.: WO2016/063926
PCT Pub. Date: Apr. 28, 2016

(65) Prior Publication Data
US 2018/0327448 A1  Nov. 15, 2018

(30) Foreign Application Priority Data
Oct. 22, 2014  (JP) .................. 2014-215789

(51) Int. Cl.
*C07K 1/22* (2006.01)
*C07K 7/00* (2006.01)
*C07K 7/06* (2006.01)
*C07K 7/08* (2006.01)
*B01D 15/38* (2006.01)
*C07K 14/32* (2006.01)
*C12N 15/09* (2006.01)

(52) U.S. Cl.
CPC ............ *C07K 1/22* (2013.01); *B01D 15/3819* (2013.01); *C07K 7/00* (2013.01); *C07K 14/32* (2013.01); *C07K 7/06* (2013.01); *C07K 7/08* (2013.01); *C12N 15/09* (2013.01)

(58) Field of Classification Search
None
See application file for complete search history.

(56) References Cited

U.S. PATENT DOCUMENTS

| 2007/0112174 A1 | 5/2007 | Shiba et al. |
| 2009/0098578 A1 | 4/2009 | Kuroda et al. |
| 2009/0118142 A1* | 5/2009 | Kuroda .................. C07K 14/21 506/32 |
| 2010/0029905 A1 | 2/2010 | Kuroda et al. |

FOREIGN PATENT DOCUMENTS

| CN | 1829734 A | 9/2006 |
| DK | 1661910 T3 | 12/2013 |
| EP | 1661910 A1 | 5/2006 |
| EP | 1953550 A1 | 8/2008 |
| ES | 2438190 T3 | 1/2014 |
| JP | 2009-136280 A | 6/2009 |
| JP | 2010-37222 A | 2/2010 |
| JP | 2011-219453 A | 11/2011 |
| JP | 2012-31100 A | 2/2012 |
| JP | 4885542 B2 | 2/2012 |
| JP | 5186689 B2 | 4/2013 |
| JP | 2015-40208 A | 3/2015 |
| WO | 2005/010031 A1 | 2/2005 |
| WO | 2007/055288 A1 | 5/2007 |
| WO | 2012/090789 A1 | 7/2012 |

OTHER PUBLICATIONS

Chen et al. QCM-D Analysis of Binding Mechanism of Phage Particles Displaying a Constrained Heptapeptide with Specific Affinity to SiO2 and TiO2. Anal Chem, 2006, vol. 78, pp. 4872-4879 (Year: 2006).*
Abdelhamid et al., "Affinity Purification of Recombinant Proteins Using a Novel Silica-Binding Peptide as a Fusion Tag", Applied Microbiology and Biotechnology, vol. 98, 2014, pp. 5677-5684.
International Preliminary Report on Patentability received for PCT Patent Application No. PCT/JP2015/079753, completed on Jan. 20, 2017 20 pages (10 pages of English Translation and 10 pages of Official Copy).
International Search Report received for PCT Patent Application No. PCT/JP2015/079753, dated Jan. 26, 2016, 6 pages (2 page of English Translation and 4 pages of Official Copy).
Written Opinion received for PCT Patent Application No. PCT/JP2015/079753, dated Jan. 26, 2016, 5 pages (Official Copy Only) (See Communication under 37 CFR § 1.98(a) (3)).
Abdelhamid et al., "Affinity Purification of Recombinant Proteins using a Novel Silica-Binding Peptide as a Fusion Tag", Applied Microbiology and Biotechnology, Apr. 23, 2014, Supplementary Materials, 3 pages.
Extended European Search Report (includes Supplementary European Search Report and Search Opinion) received for European Patent Application No. 15853595.5, dated Nov. 27, 2017, 7 pages.

* cited by examiner

*Primary Examiner* — Marcela M Cordero Garcia
(74) *Attorney, Agent, or Firm* — Morrison & Foerster LLP

(57) ABSTRACT

The present invention provides a method for purifying an intended substance, a kit for purifying the intended substance, and a silicon oxide-binding tag for use in the method and the kit. In the present invention, a complex of a silicon oxide-binding tag and a substance is caused to specifically bind to silicon oxide in a solution for binding, to which solution no salt is added, and binding between the silicon oxide-binding tag and the silicon oxide is broken with use of arginine.

13 Claims, 5 Drawing Sheets
Specification includes a Sequence Listing.

SEQUENCE LISTING

```
<160> NUMBER OF SEQ ID NOS: 23

<210> SEQ ID NO 1
<211> LENGTH: 14
<212> TYPE: PRT
<213> ORGANISM: Artificial Sequence
<220> FEATURE:
<223> OTHER INFORMATION: Artificially Synthesized Sequence

<400> SEQUENCE: 1

Ser Gly Arg Ala Arg Ala Gln Arg Gln Ser Ser Arg Gly Arg
1               5                   10

<210> SEQ ID NO 2
<211> LENGTH: 42
<212> TYPE: DNA
<213> ORGANISM: Artificial Sequence
<220> FEATURE:
<223> OTHER INFORMATION: Artificially Synthesized Sequence

<400> SEQUENCE: 2
tcaggtcgtg ctcgtgcaca aagacaatca agtagaggaa ga                           42

<210> SEQ ID NO 3
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 3
```

Arg Gln Ser Ser Arg Gly Arg
1               5

<210> SEQ ID NO 4
<211> LENGTH: 21
<212> TYPE: DNA
<213> ORGANISM: Artificial Sequence
<220> FEATURE:
<223> OTHER INFORMATION: Artificially Synthesized Sequence

<400> SEQUENCE: 4
agacaatcaa gtagaggaag a                                          21

<210> SEQ ID NO 5
<211> LENGTH: 10
<212> TYPE: PRT
<213> ORGANISM: Artificial Sequence
<220> FEATURE:
<223> OTHER INFORMATION: Artificially Synthesized Sequence

<400> SEQUENCE: 5

Arg Ala Gln Arg Gln Ser Ser Arg Gly Arg
1               5                   10

<210> SEQ ID NO 6
<211> LENGTH: 30
<212> TYPE: DNA
<213> ORGANISM: Artificial Sequence
<220> FEATURE:
<223> OTHER INFORMATION: Artificially Synthesized Sequence

<400> SEQUENCE: 6
cgtgcacaaa gacaatcaag tagaggaaga                                 30

<210> SEQ ID NO 7
<211> LENGTH: 8
<212> TYPE: PRT
<213> ORGANISM: Artificial Sequence
<220> FEATURE:
<223> OTHER INFORMATION: Artificially Synthesized Sequence

<400> SEQUENCE: 7

Ser Gly Arg Ala Arg Ala Gln Arg
1               5

<210> SEQ ID NO 8
<211> LENGTH: 24
<212> TYPE: DNA
<213> ORGANISM: Artificial Sequence
<220> FEATURE:
<223> OTHER INFORMATION: Artificially Synthesized Sequence

<400> SEQUENCE: 8
tcaggtcgtg ctcgtgcaca aaga                                       24

<210> SEQ ID NO 9
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 9

Ala Gln Ser Ser Arg Gly Arg
1               5

```
<210> SEQ ID NO 10
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 10

Arg Ala Ser Ser Arg Gly Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 11

Arg Gln Ala Ser Arg Gly Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 12

Arg Gln Ser Ala Arg Gly Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 13

Arg Gln Ser Ser Ala Gly Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 14

Arg Gln Ser Ser Arg Ala Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Artificially Synthesized Sequence

<400> SEQUENCE: 15

Arg Gln Ser Ser Arg Gly Ala
1               5

<210> SEQ ID NO 16
```

<211> LENGTH: 9
<212> TYPE: PRT
<213> ORGANISM: Artificial Sequence
<220> FEATURE:
<223> OTHER INFORMATION: Artificially Synthesized Sequence

<400> SEQUENCE: 16

Arg Arg Arg Arg Arg Arg Arg Arg Arg
1               5

<210> SEQ ID NO 17
<211> LENGTH: 27
<212> TYPE: DNA
<213> ORGANISM: Artificial Sequence
<220> FEATURE:
<223> OTHER INFORMATION: Artificially Synthesized Sequence

<400> SEQUENCE: 17
cgtcgccgtc gtcgccgtcg tcgtcgc     27

<210> SEQ ID NO 18
<211> LENGTH: 273
<212> TYPE: PRT
<213> ORGANISM: Artificial Sequence
<220> FEATURE:
<223> OTHER INFORMATION: Artificially Synthesized Sequence

<400> SEQUENCE: 18

Met Ala Val Val Lys Cys Lys Pro Thr Ser Pro Gly Arg Arg His Val
1               5                   10                  15

Val Lys Val Val Asn Pro Glu Leu His Lys Gly Lys Pro Phe Ala Pro
                20                  25                  30

Leu Leu Glu Lys Asn Ser Lys Ser Gly Gly Arg Asn Asn Asn Gly Arg
            35                  40                  45

Ile Thr Thr Arg His Ile Gly Gly His Lys Gln Ala Tyr Arg Ile
        50                  55                  60

Val Asp Phe Lys Arg Asn Lys Asp Gly Ile Pro Ala Val Val Glu Arg
65                  70                  75                  80

Leu Glu Tyr Asp Pro Asn Arg Ser Ala Asn Ile Ala Leu Val Leu Tyr
                85                  90                  95

Lys Asp Gly Glu Arg Arg Tyr Ile Leu Ala Pro Lys Gly Leu Lys Ala
            100                 105                 110

Gly Asp Gln Ile Gln Ser Gly Val Asp Ala Ala Ile Lys Pro Gly Asn
        115                 120                 125

Thr Leu Pro Met Arg Asn Ile Pro Val Gly Ser Thr Val His Asn Val
    130                 135                 140

Glu Met Lys Pro Gly Lys Gly Gly Gln Leu Ala Arg Ser Ala Gly Thr
145                 150                 155                 160

Tyr Val Gln Ile Val Ala Arg Asp Gly Ala Tyr Val Thr Leu Arg Leu
                165                 170                 175

Arg Ser Gly Glu Met Arg Lys Val Glu Ala Asp Cys Arg Ala Thr Leu
            180                 185                 190

Gly Glu Val Gly Asn Ala Glu His Met Leu Arg Val Leu Gly Lys Ala
        195                 200                 205

Gly Ala Ala Arg Trp Arg Gly Val Arg Pro Thr Val Arg Gly Thr Ala
    210                 215                 220

Met Asn Pro Val Asp His Pro His Gly Gly Gly Glu Gly Arg Asn Phe
225                 230                 235                 240

Gly Lys His Pro Val Thr Pro Trp Gly Val Gln Thr Lys Gly Lys Lys 245                 250                 255
Thr Arg Ser Asn Lys Arg Thr Asp Lys Phe Ile Val Arg Arg Ser
            260                 265                 270
Lys

<210> SEQ ID NO 19
<211> LENGTH: 822
<212> TYPE: DNA
<213> ORGANISM: Artificial Sequence
<220> FEATURE:
<223> OTHER INFORMATION: Artificially Synthesized Sequence

<400> SEQUENCE: 19
atggcagttg ttaaatgtaa accgacatct ccgggtcgtc gccacgtagt taaagtggtt    60
aaccctgagc tgcacaaggg caaaccttt gctccgttgc tggaaaaaaa cagcaaatcc   120
ggtggtcgta acaacaatgg ccgtatcacc actcgtcata tcggtggtgg ccacaagcag   180
gcttaccgta tgttgactt caaacgcaac aaagacggta cccgggcagt tgttgaacgt   240
cttgagtacg atccgaaccg ttccgcgaac atcgcgctgg ttctgtacaa agacggtgaa   300
cgccgttaca tcctggcccc taaaggcctg aaagctggcg accagattca gtctggcgtt   360
gatgctgcaa tcaaaccagg taacaccctg ccgatgcgca acatcccggt tggttctact   420
gttcataacg tagaaatgaa accaggtaaa ggcggtcagc tggcacgttc cgctggtact   480
tacgttcaga tcgttgctcg tgatggtgct tatgtcaccc tgcgtctgcg ttctggtgaa   540
atgcgtaaag tagaagcaga ctgccgtgca actctgggcg aagttggcaa tgctgagcat   600
atgctgcgcg ttctgggtaa agcaggtgct gcacgctggc gtggtgttcg tccgaccgtt   660
cgcggtaccg cgatgaaccc ggtagaccac ccacatggtg gtggtgaagg tcgtaacttt   720
ggtaagcacc cggtaactcc gtggggcgtt cagaccaaag gtaagaagac ccgcagcaac   780
aagcgtactg ataaattcat cgtacgtcgc cgtagcaaat aa                      822

<210> SEQ ID NO 20
<211> LENGTH: 13
<212> TYPE: PRT
<213> ORGANISM: Artificial Sequence
<220> FEATURE:
<223> OTHER INFORMATION: Artificially Synthesized Sequence

<400> SEQUENCE: 20

Gly Arg Lys Lys Arg Arg Gln Arg Arg Pro Pro Gln
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Artificially Synthesized Sequence

<400> SEQUENCE: 21

Tyr Gly Arg Lys Lys Arg Arg Gln Arg Arg Arg
1               5                   10

<210> SEQ ID NO 22
<211> LENGTH: 236
<212> TYPE: PRT
<213> ORGANISM: Artificial Sequence
<220> FEATURE:
<223> OTHER INFORMATION: Artificially Synthesized Sequence

<400> SEQUENCE: 22

```
Met Val Ser Lys Gly Glu Glu Asp Asn Met Ala Ile Ile Lys Glu Phe
1               5                   10                  15
Met Arg Phe Lys Val His Met Glu Gly Ser Val Asn Gly His Glu Phe
                20                  25                  30
Glu Ile Glu Gly Glu Gly Glu Gly Arg Pro Tyr Glu Gly Thr Gln Thr
            35                  40                  45
Ala Lys Leu Lys Val Thr Lys Gly Gly Pro Leu Pro Phe Ala Trp Asp
    50                  55                  60
Ile Leu Ser Pro Gln Phe Met Tyr Gly Ser Lys Ala Tyr Val Lys His
65                  70                  75                  80
Pro Ala Asp Ile Pro Asp Tyr Leu Lys Leu Ser Phe Pro Glu Gly Phe
                85                  90                  95
Lys Trp Glu Arg Val Met Asn Phe Glu Asp Gly Gly Val Val Thr Val
            100                 105                 110
Thr Gln Asp Ser Ser Leu Gln Asp Gly Glu Phe Ile Tyr Lys Val Lys
    115                 120                 125
Leu Arg Gly Thr Asn Phe Pro Ser Asp Gly Pro Val Met Gln Lys Lys
130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
            180                 185                 190
Gln Leu Pro Gly Ala Tyr Asn Val Asn Ile Lys Leu Asp Ile Thr Ser
    195                 200                 205
His Asn Glu Asp Tyr Thr Ile Val Glu Gln Tyr Glu Arg Ala Glu Gly
210                 215                 220
Arg His Ser Thr Gly Gly Met Asp Glu Leu Tyr Lys
225                 230                 235
```

<210> SEQ ID NO 23
<211> LENGTH: 168
<212> TYPE: PRT
<213> ORGANISM: Bacillus subtilis

<400> SEQUENCE: 23

```
Met Ile Ser Phe Ile Phe Ala Met Asp Ala Asn Arg Leu Ile Gly Lys
1               5                   10                  15
Asp Asn Asp Leu Pro Trp His Leu Pro Asn Asp Leu Ala Tyr Phe Lys
                20                  25                  30
Lys Ile Thr Ser Gly His Ser Ile Ile Met Gly Arg Lys Thr Phe Glu
            35                  40                  45
Ser Ile Gly Arg Pro Leu Pro Asn Arg Lys Asn Ile Val Val Thr Ser
    50                  55                  60
Ala Pro Asp Ser Glu Phe Gln Gly Cys Thr Val Ser Ser Leu Lys
65                  70                  75                  80
Asp Val Leu Asp Ile Cys Ser Gly Pro Glu Glu Cys Phe Val Ile Gly
                85                  90                  95
Gly Ala Gln Leu Tyr Thr Asp Leu Phe Pro Tyr Ala Asp Arg Leu Tyr
            100                 105                 110
Met Thr Lys Ile His His Glu Phe Glu Gly Asp Arg His Phe Pro Glu
            115                 120                 125
```

```
                                        -continued

Phe Asp Glu Ser Asn Trp Lys Leu Val Ser Ser Glu Gln Gly Thr Lys
    130                 135                 140

Asp Glu Lys Asn Pro Tyr Asp Tyr Glu Phe Leu Met Tyr Glu Lys Lys
145                 150                 155                 160

Asn Ser Ser Lys Ala Gly Gly Phe
                165
```

PURIFICATION METHOD, PURIFICATION KIT, AND SILICON OXIDE-BINDING TAG FOR USE THEREIN

CROSS-REFERENCE TO RELATED APPLICATIONS

This application is a U.S. National Phase Patent Application of PCT/JP2015/079753, filed Oct. 21, 2015, which claims priority to Japanese Patent Application No. 2014-215789, filed Oct. 22, 2014, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 247322020100SeqList.txt, date recorded: Apr. 20, 2017, size: 12 KB).

FIELD

The present invention relates to a purification method, a purification kit, and a silicon oxide-binding tag for the purification method and the purification kit.

BACKGROUND ART

In recent years, many proteins related to silicon oxide have been discovered, and attempts are made to put the proteins to various uses (e.g., a technique of polymerizing silicon oxide, a technique of fixing a desired substance on silicon oxide, and a technique of purifying a desired substance fixed on silicon oxide).

For example, Patent Literature 1 discloses a particular protein (CotG protein) derived from *Bacillus* bacteria, and a polypeptide of a fragment of the protein. In the technique disclosed in Patent Literature 1, silica is polymerized with use of the protein and a fragment of the protein.

Patent Literature 2 discloses a particular protein (SBP: silica material binding protein) which is capable of binding to silicon oxide (e.g., silica), and a tag derived from the protein. In the technique disclosed in Patent Literature 2, a fusion protein of a tag and a desired protein is used so that the desired protein is fixed on silicon oxide via the tag.

Patent Literature 3 discloses a particular protein (SBP: silica material binding protein) which is capable of binding to silicon oxide (e.g., silica), and a tag derived from the protein. In the technique disclosed in Patent Literature 3, a fusion protein of a tag and a desired protein is used so that the desired protein is fixed on silicon oxide via the tag, and further with use of a divalent cation-containing solution, the desired protein is dissociated from the silicon oxide.

Patent Literature 4 discloses a peptide which is capable of binding to silicon dioxide. In the technique disclosed in Patent Literature 4, a fusion protein of a peptide and a desired protein is used so that the desired protein is fixed on silicon dioxide via the peptide, and further with use of an arginine-containing solution, the desired protein is dissociated from the silicon dioxide.

Note that in conventional techniques, in order to prevent a protein other than an intended fusion protein from being adsorbed nonspecifically on silicon oxide or silicon dioxide, the fusion protein is fixed on silicon oxide or silicon dioxide in a solution containing a salt in high concentration. Further, in the conventional techniques, the use of the solution containing the salt in high concentration enables purification of a high purity fusion protein.

As described above, attempts have been made to put proteins related to silicon oxide to various uses, among which the technique of purifying a desired substance fixed on silicon oxide is particularly attracting a great interest, and early development of the technique is hoped for. For the technique, it is important to discover not only a tag capable of binding to silicon oxide, but also a method for causing a tag which is bound to silicon oxide to be specifically dissociated from the silicon oxide.

CITATION LIST

Patent Literature

Patent Literature 1

Japanese Patent Application Publication, Tokukai, No. 2012-31100 A (Publication Date: Feb. 16, 2012)

Patent Literature 2

International Publication No. WO2007/055288 (Publication Date: May 18, 2007)

Patent Literature 3

Japanese Patent Application Publication, Tokukai, No. 2010-37222 A (Publication Date: Feb. 18, 2010)

Patent Literature 4

Japanese Patent Application Publication, Tokukai, No. 2009-136280 A (Publication Date: Jun. 25, 2009)

SUMMARY OF INVENTION

Technical Problem

As described above, in the technique disclosed in Patent Literature 3, a particular tag which is bound to silicon oxide is dissociated from the silicon oxide with use of a divalent cation-containing solution.

However, the technique has a problem that a substance (in particular, a protein) to be purified may be denatured by a divalent cation.

As such, in the technical field, there is a great demand for discovery of a novel combination of a tag and a method that allows the tag which is bound to silicon oxide to be specifically dissociated from the silicon oxide.

The present invention is accomplished in view of the foregoing problem. An object of the present invention is to provide: a method for purifying an intended substance with use of (i) a silicon oxide-binding tag and (ii) a method of specifically dissociating the silicon oxide-binding tag from silicon oxide; and the silicon oxide-binding tag used in the purification method.

Solution to Problem

Through study of a mechanism by which a prokaryote (e.g., *Bacillus cereus*) takes silicic acid into the body of the prokaryote, the inventors of the present invention discovered that (i) specific binding between silicon oxide and a protein which is derived from *Bacillus* and has a silicon oxide-binding capacity can be broken with use of arginine and (ii) by causing a complex of a silicon oxide-binding tag and a substance to bind specifically to silicon oxide in a solution for binding to which solution no salt is added, it is possible to (a) prevent an unnecessary substance other than the complex from binding to the silicon oxide and (b) accordingly purify the complex with high yield and high purity. On the basis of the discovery, the inventors accomplished the present invention.

In order to attain the object, a method, of the present invention, for purifying a complex is a method for purifying a complex, including: a binding step of causing a complex of a silicon oxide-binding tag and a substance to specifically bind to silicon oxide in a solution for binding, to which solution no salt is added; and a dissociating step of dissociating the complex from the silicon oxide, the dissociating step being a step of causing arginine to break binding between the silicon oxide-binding tag and the silicon oxide.

The method of the present invention is preferably arranged such that the solution for binding is: a solution consisting of a pH buffer solution and a solvent; or a solution consisting of a pH buffer solution, a surfactant, and a solvent.

The method of the present invention is preferably arranged such that the substance is a protein.

The method of the present invention is preferably arranged such that the dissociating step is a step of bringing the complex, which is bound to the silicon oxide, into contact with an eluate containing arginine; and the eluate contains only the arginine as a dissociating agent for breaking specific binding between the silicon oxide-binding tag and the silicon oxide.

The method of the present invention is preferably arranged such that the silicon oxide is contained in *Shirasu*.

The method of the present invention is preferably arranged such that the silicon oxide-binding tag contains a polypeptide; and not less than 5/14 and less than 7/7 of all amino acids constituting the polypeptide are arginine.

The method of the present invention is preferably arranged such that the polypeptide has not more than 14 amino acids.

The method of the present invention is preferably arranged such that the polypeptide includes, as at least part thereof, a polypeptide of (a) or (b): (a) a polypeptide having an amino acid sequence of SEQ ID NO: 1, 3, 5, 20, or 21; and (b) a polypeptide having an amino acid sequence of SEQ ID NO: 1, 3, 5, 20 or 21 in which one or several amino acids are deleted, substituted, or added, the polypeptide having a silicon oxide-binding capacity.

In order to attain the object, a silicon oxide-binding tag of the present invention is a silicon oxide-binding tag containing a polypeptide having not more than seven amino acids, not less than 3/7 and less than 7/7 of all amino acids constituting the polypeptide being arginine.

The silicon oxide-binding tag of the present invention is preferably configured such that the polypeptide includes, as at least part thereof, a polypeptide of (c) or (d): (c) a polypeptide having an amino acid sequence of SEQ ID NO: 3; and (d) a polypeptide having an amino acid sequence of SEQ ID NO: 3 in which one or several amino acids are deleted, substituted, or added, the polypeptide having a silicon oxide-binding capacity.

In order to attain the object, a kit of the present invention is a kit for purifying a complex of a silicon oxide-binding tag and a substance, including: a column which contains silicon oxide as a stationary phase for separation; a silicon oxide-binding tag which binds to the silicon oxide; a solution for binding, to which solution no salt is added and which solution is for causing the complex to specifically bind to the silicon oxide; and a solution for dissociation, which solution contains arginine and is for breaking binding between the silicon oxide-binding tag and the silicon oxide.

Advantageous Effects of Invention

The present invention enables purification of an intended substance with high purity.

The present invention enables purification of an intended substance at a high recovery rate.

The present invention allows designing a silicon oxide-binding tag having a small size. Accordingly, by linking the silicon oxide-binding tag with a desired substance (e.g., a polymer such as a protein), it is possible to prevent a significant change in structure of the desired substance. In other words, the present invention allows preventing a desired substance (e.g., a polymer such as a protein) from losing a function (e.g., an enzyme activity) when the silicon oxide-binding tag is linked with the desired substance.

The present invention allows inexpensive silica particles to be used as a carrier for purification. Accordingly, the present invention makes it possible to provide a low-cost purification method.

Arginine has an effect (i.e., an aggregation suppression effect) of stabilizing a structure of an intended substance (e.g., a protein). Accordingly, the present invention allows the intended substance to be purified without loss of a function (e.g., an enzyme activity).

Due to having a low molecular weight, arginine can be removed easily by dialysis or the like. Accordingly, the present invention allows arginine to be removed easily from a purified product.

DESCRIPTION OF EMBODIMENTS

Figure 1:
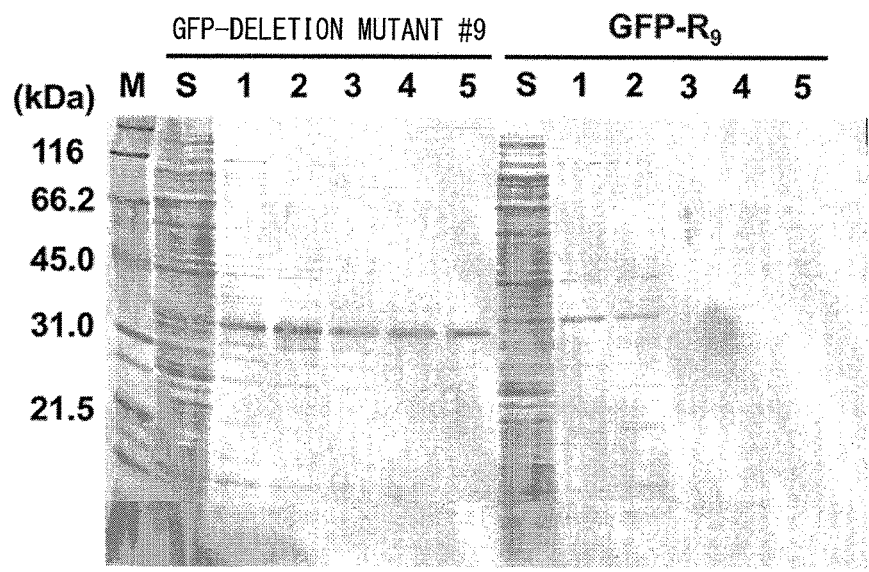
FIG. 1 is an image of a gel in SDS-PAGE, the image showing results of a test in an example of the present invention.

An embodiment of the present invention is described below. Note, however, that the present invention is not limited to such an embodiment. The present invention is not limited to arrangements described below, but can be altered by a skilled person in the art within the scope of the claims. An embodiment or example derived from a proper combination of technical means each disclosed in a different embodiment or example is also encompassed in the technical scope of the present invention. All academic and patent literatures listed herein are incorporated herein by reference. Note that a numerical range "A to B" herein means "not less than A and not more than B" unless otherwise specified.

<1. Purification Method>

Conventionally, there has been a technique in which arginine is added to an eluate which is used in eluting a protein from a column (e.g., (1) Tsutomu Arakawa et al., Protein Expression and Purification, 36 (2004) 244-248, (2) Daisuke Ejima et al., Analytical Biochemistry 345 (2005) 250-257, and (3) Tsutomu Arakawa et al., Protein Expression and Purification, 54 (2007) 110-116). However, such conventional techniques completely differ from the present invention in technical idea (specifically, a role of arginine). This point will be detailed first.

In the present invention, a complex specifically binds to silicon oxide via a silicon oxide-binding body. Further, in the present invention, the specific binding is broken with use of arginine, so that the complex is eluted from a column. That is, the present invention employs arginine as a dissociating agent which is used for eluting the complex from the column.

Meanwhile, it has been conventionally known that arginine stabilizes a structure of a protein. As such, in the conventional techniques described above, arginine is also used as a stabilizer for simply preventing a protein from being denatured etc. when the protein is eluted.

Specifically, the conventional techniques disclosed in (1) and (2) above use citric acid (i.e., an acidic solution) as a dissociating agent, and arginine as a stabilizer for a protein. The technique disclosed in (3) above uses ammonium sulfate as a dissociating agent, and arginine as a stabilizer for a protein.

Thus, the present invention is completely different from the conventional techniques in role of arginine. Regarding the conventional techniques, there has been neither a report nor a technical idea that arginine is capable of dissociating a silicon oxide binding body from silicon oxide.

Furthermore, conventionally, in order to prevent an unnecessary substance from binding to a column when a substance to be purified is caused to bind to the column, the substance to be purified is caused to bind to a carrier in a solution for binding, to which solution a salt has been intentionally added. As a result, the substance to be purified is purified with increased purity.

However, as discussed in the Examples (described later), in a case of using silicon oxide as a stationary phase for separation in a column, a higher concentration of a salt contained in the solution for binding causes more unnecessary substances to bind to the column, thus resulting in a decreased purity with which the substance to be purified is purified. This is unique new knowledge obtained by the inventors of the present invention.

In the present invention, a solution for binding, to which solution no salt is added, is used, so that a substance to be purified can be purified with high purity and at a high recovery rate.

The following will discuss in detail an embodiment of a purification method of the present invention.

A purification method, of the present embodiment, for purifying a complex includes: a binding step of causing a complex of a silicon oxide-binding tag and a substance to specifically bind to silicon oxide in a solution for binding, to which solution no salt is added; and a dissociating step of dissociating the complex from the silicon oxide, the dissociating step being a step of causing arginine to break binding between the silicon oxide-binding tag and the silicon oxide.

As used herein, the term "a binding solution to which no salt is added (i.e., a binding solution containing no salt)" means a solution to which no salt (e.g., NaCl, KCl, or ammonium sulfate) intended to prevent an unnecessary substance other than a complex from nonspecifically binding to silicon oxide is intentionally added.

In some cases, for example, (i) a salt is contained in a substance (e.g., a pH buffer solution, a surfactant, a reducing agent, or a chelating agent) which is not intended to prevent an unnecessary substance other than a complex from nonspecifically binding to silicon oxide and which is for adjusting properties of a binding solution into desired properties and (ii) as a result of adding such a substance to the binding solution, the binding solution comes to contain the salt. Such a binding solution is within the scope of "a binding solution to which no salt is added" of the present invention.

Further, in a case of producing a complex with use of a living organism (e.g., in a case where an expression vector into which a polynucleotide encoding a complex is introduced into a microorganism such as *Escherichia coli* or yeast, so that the complex is expressed in the microorganism), a lysate obtained by disrupting the living organism can be used as a binding solution. In this case, the binding solution, which contains a salt derived from the living organism, is also within the scope of "a binding solution to which no salt is added" of the present invention.

Specific examples of the binding solution to which no salt is added encompass: a solution consisting of a pH buffer solution and a solvent; or a solution consisting of a pH buffer solution, a surfactant, and a solvent.

More specific examples of a pH buffer solution encompass a Tris-HCl buffer solution, a phosphate buffer solution, a HEPES buffer solution, a MOPS buffer solution, and a citric acid buffer solution. More specific examples of a surfactant encompass Tween 20 (registered trademark), Tween 80 (registered trademark), Triton X-100 (registered trademark), n-octyl glucoside, and CHAPS. More specific examples of a solvent encompass water, acetonitrile, DMSO, glycerol, and a mixture thereof. Note, however, that the present invention is not limited to these examples.

As described above, the binding solution may contain a salt derived from a substance which is not intended to prevent an unnecessary substance other than a complex from nonspecifically binding to silicon oxide and which is for adjusting the properties of the binding solution into desired properties. Even in this case, a concentration of the salt contained in the binding solution is preferably as low as possible from a viewpoint of increasing the purity with which the complex is purified.

The concentration of the salt contained in the binding solution is, for example, preferably 0 mM to 100 mM, more preferably 0 mM to 80 mM, more preferably 0 mM to 60 mM, more preferably 0 mM to 40 mM, more preferably 0 mM to 20 mM, and most preferably 0 mM.

The silicon oxide-binding tag is a tag having a capacity to bind to silicon oxide (e.g., silicon dioxide (silica), quartz, cristobalite, silica gel, and the like). Accordingly, by linking the silicon oxide-binding tag and a desired substance with each other (a product obtained by linking the silicon oxide-binding tag and the substance with each other may also be referred to as a complex of the silicon oxide-binding tag and the substance), it is possible to cause the desired substance to bind to silicon oxide via the silicon oxide-binding tag. Then, in the purification method of the present embodiment, specific binding between the silicon oxide-binding tag and silicon oxide is broken with use of arginine.

Silicon oxide to which the silicon oxide-binding tag binds is not limited a particular configuration, but is preferably silicon oxide contained in Shirasu (i.e., a mixture of volcanic ash and pumice). In other words, Shirasu may be used instead of silicon oxide in the purification method of the present embodiment. This configuration allows a complex of the silicon oxide-binding tag and the substance to be purified with high purity and at a high recovery rate. Further, the configuration allows providing a low-cost purification method. Note that "Shirasu" is particles of pumice and volcanic ash which are distributed throughout southern Kyushu, Japan, and contains silicon oxide as a component.

The "silicon oxide-binding capacity" described above can be measured by bringing an excess amount of silicon oxide (e.g., silicon oxide which is 1000 times greater in mass than the silicon oxide-binding tag) and the silicon oxide-binding tag into contact with each other in a desired aqueous solution at room temperature for 30 minutes and measuring an amount of the silicon oxide-binding tag which binds to the silicon oxide.

For example, in a case where preferably not less than 5%, more preferably not less than 10%, more preferably not less than 20%, more preferably not less than 30%, more preferably not less than 40%, and most preferably not less than 50% of the silicon oxide-binding tag successfully binds to silicon oxide, the peptide is determined as having a silicon oxide-binding capacity.

A specific percentage by which the silicon oxide-binding tag has bound to silicon oxide can be determined, for example, by (i) bringing silicon oxide and the silicon oxide-binding tag into contact with each other, (ii) fractionating the silicon oxide and the silicon oxide-binding tag, which are thus in contact with each other, into a supernatant and a precipitate by centrifugal separation, (iii) subjecting the supernatant and the precipitate to SDS-PAGE, and (iv) then staining a gel, which is used in the SDS-PAGE, by a desired method so that bands, which are observed in the gel and correspond to the silicon oxide-binding tag, are compared with each other.

Examples of an aqueous solution used in bringing the excess amount of silicon oxide and the silicon oxide-binding tag into contact with each other encompass 25 mM Tris-HCl buffer solution (pH 8.0). Further, the aqueous solution used in bringing the excess amount of silicon oxide and the silicon oxide-binding tag into contact with each other may be 25 mM Tris-HCl buffer solution (pH 8.0) containing a surfactant (e.g., polyoxyethylene sorbitan monolaurate (more specifically, Tween 20 (registered trademark))).

Binding which is maintained between the silicon oxide-binding tag and silicon oxide in 25 mM Tris-HCl buffer solution (pH 8.0) is herein defined as "specific binding". Further, binding maintained between the silicon oxide-binding tag and silicon oxide in 25 mM Tris-HCl buffer solution (pH 8.0) containing a surfactant (e.g., polyoxyethylene sorbitan monolaurate (more specifically, Tween 20 (registered trademark))) is herein defined as "more specific binding" among "specific bindings."

A concentration of the surfactant in the aqueous solution is, for example, preferably 0.05% (v/v), more preferably 0.1% (v/v), more preferably 0.5% (v/v), more preferably 1.0% (v/v), and most preferably 1.5% (v/v).

The silicon oxide-binding tag may be any silicon oxide-binding tag provided that (i) the silicon oxide-binding tag has a silicon oxide-binding capacity and (ii) specific binding between the silicon oxide-binding tag and silicon oxide is broken with use of arginine. The silicon oxide-binding tag is not limited to a particular configuration.

For example, the silicon oxide-binding tag preferably contains a polypeptide.

In a case where the silicon oxide-binding tag contains a polypeptide, an amino acid constituting the polypeptide is not limited to a particular kind. However, preferably not less than 5/14 and less than 7/7, more preferably not less than 5/14 and less than 6/7, more preferably not less than 5/14 and less than 5/7, more preferably not less than 5/14 and less than 4/7, and most preferably not less than 5/14 and less than 3/7, of all amino acids constituting the polypeptide are arginine. This configuration not only allows the silicon oxide-binding tag to bind to silicon oxide efficiently, but also allows binding between the silicon oxide-binding tag and silicon oxide to be efficiently broken by arginine. Meanwhile, in a case where less than 5/14 of all amino acids constituting the silicon oxide-binding tag are arginine and in a case where all amino acids constituting the silicon oxide-binding tag are arginine, an efficiency of binding of the silicon oxide-binding tag to silicon oxide tends to decrease.

In a case where the silicon oxide-binding tag contains a polypeptide, the number of amino acids constituting the polypeptide is not limited, but preferably not more than 100, more preferably not more than 90, more preferably not more than 80, more preferably not more than 70, more preferably not more than 60, more preferably not more than 50, more preferably not more than 40, more preferably not more than 30, more preferably not more than 20, more preferably not more than 14, more preferably not more than 10, and most preferably not more than seven.

As a size of the silicon oxide-binding tag decreases, a significant change in structure of a desired substance can be prevented more when the silicon oxide-binding tag is linked with the desired substance. In other words, a decrease in size of the silicon oxide-binding tag allows further preventing a desired substance (e.g., a polymer such as a protein) from losing a function (e.g., an enzyme activity) when the silicon oxide-binding tag is linked with the desired substance. Further, a decrease in size of the silicon oxide-binding tag allows a complex of the silicon oxide-binding tag and a desired substance to have a greater solubility in an aqueous solution when the silicon oxide-binding tag is linked with the desired substance. From these viewpoints, in a case where the silicon oxide-binding tag contains a polypeptide, the number of amino acids constituting the polypeptide is preferably not more than 14 and more preferably not more than seven.

The polypeptide constituting the silicon oxide-binding tag may contain, as at least part of the polypeptide, a polypeptide of (a) or (b) or may consist of the polypeptide of (a) or (b):

(a) a polypeptide having an amino acid sequence of SEQ ID NO: 1, 3, 5, 20, or 21; and (b) a polypeptide having an amino acid sequence of SEQ ID NO: 1, 3, 5, 20, or 21 in which one or several amino acids are deleted, substituted, or added, the polypeptide having a silicon oxide-binding capacity.

Note here that a polypeptide having amino acids of SEQ ID NOs: 1, 3, and 5 is a partial peptide of a CotB1 protein derived from *Bacillus cereus* (e.g., *Bacillus cereus* ATCC 14579), which is a prokaryote.

A polypeptide having amino acid sequences of SEQ ID NOs: 20 and 21 (an amino acid sequence of SEQ ID NO: 20: GRKKRRQRRRPPQ, and an amino acid sequence of SEQ ID NO: 21: YGRKKRRQRRR) is a partial peptide of a TAT (Transactivator of transcription) protein involved in control of transcription of a human immunodeficiency virus. The partial peptide is identified as an intracellular transfer peptide having a function of enabling transfer of the TAT protein into cells.

The polypeptide of (b) above is preferably a polypeptide which (i) has an amino acid sequence of SEQ ID NO: 1, 3, 5, 20, or 21 in which one or several amino acids other than arginine are deleted, substituted, or added and (ii) has a silicon oxide-binding capacity. This configuration not only allows the silicon oxide-binding tag to bind to silicon oxide efficiently but also allows binding between the silicon oxide-binding tag and silicon oxide to be efficiently broken by arginine.

The term "one or several amino acids are deleted, substituted, or added" in the peptide of (b) above means that a certain number (preferably not more than nine, more preferably not more than eight, more preferably not more than seven, more preferably not more than six, more preferably not more than five, more preferably not more than four, more preferably not more than three, more preferably not more than two, and most preferably not more than one) of amino acids, in which number the amino acids can be deleted, substituted, or added by a known mutant peptide production method such as site-directed mutagenesis, are deleted, substituted, or added.

The peptide of (b) above may be a polypeptide which (i) has an amino acid sequence having a sequence identity of preferably not less than 30%, more preferably not less than 35%, more preferably not less than 40%, more preferably not less than 45%, more preferably not less than 50%, more preferably not less than 60%, more preferably not less than 70%, more preferably not less than 80%, more preferably not less than 90%, more preferably not less than 95%, more preferably not less than 96%, more preferably not less than 97%, more preferably not less than 98%, and most preferably not less than 99% with respect to an amino acid sequence of SEQ ID NO: 1, 3, 5, 20, or 21 and (ii) has a silicon oxide-binding capacity.

A sequence identity of an amino acid sequence can be determined by a known method. Specifically, for example, homology search between a particular amino acid sequence and a comparative amino acid sequence with use of GENETYX-WIN (produced by GENETYX CORPORATION) in accordance with a manual for GENETYX-WIN can be conducted so as to calculate a sequence identity as a ratio of identical amino acids (%). More specifically, the sequence identity can be calculated as a ratio of the number of identical amino acids to a total number of amino acids in a longer one of the amino acid sequences which are compared with each other.

It is known in the technical field that some amino acids in an amino acid sequence of a polypeptide can easily be modified without significantly affecting a structure or function of the polypeptide. Further, apart from the artificial modification, it is also known that in a natural polypeptide, a mutant which does not cause a significant change in structure or function of the polypeptide exists.

Examples of preferable mutation encompass substitution, deletion, or addition of an amino acid. Among these examples of mutation, the substitution of an amino acid is particularly preferable.

The substitution of an amino acid is not particularly limited, but may be such substitution in which a given amino acid is substituted with glycine or alanine. More specifically, the substitution of an amino acid may be such substitution in which serine, glycine, alanine, or glutamine is substituted with glycine or alanine. Of course, the present invention is not limited to these examples of substitution.

The silicon oxide-binding tag may be produced easily in accordance with a given method which is known in the field. For example, in a case where the silicon oxide-binding tag contains a polypeptide, the polypeptide may be produced by chemical synthesis or genetic engineering. Examples of a method of chemical synthesis encompass a solid phase method or a liquid phase method. In the solid phase method, for example, various commercially available peptide synthesizing apparatuses (such as Model MultiPep RS (Intavis AG)) can be used. In a case of producing the silicon oxide-binding tag by genetic engineering, an expression system employing a prokaryote (e.g., *Escherichia coli* and the like) or a eukaryote (e.g., yeast and the like) can be used.

A substance (i.e., a substance to be purified) with which the silicon oxide-binding tag described above is linked is not particularly limited, and may be a desired substance. Examples of the substance encompass a polypeptide (i.e., a protein), nucleic acid, sugar, a low-molecular compound, a high-molecular compound, or the like, among which a polypeptide (i.e., a protein) is particularly preferable.

A method for linking the silicon oxide-binding tag with the substance is not particularly limited, and a desired method can be used as appropriate. For example, a known cross-linking agent (i.e., a linker) can be used to link the silicon oxide-binding tag with the substance.

In a case where the silicon oxide-binding tag contains a polypeptide and the substance with which the silicon oxide-binding tag is linked is a polypeptide, the silicon oxide-binding tag and the substance (polypeptide) may be produced as a single fusion protein. In this case, the silicon oxide-binding tag may be provided (i) at the amino-terminus of the substance (polypeptide), (ii) inside the substance (polypeptide), or (iii) at the carboxyl-terminus of the substance (polypeptide). From a viewpoint of maintaining a structure of the substance (polypeptide) stable, the silicon oxide-binding tag is preferably provided at the amino-terminus or the carboxyl-terminus.

The purification method of the present embodiment includes the dissociating step of causing arginine to break specific binding between the silicon oxide-binding tag and silicon oxide. The substance with which the silicon oxide-binding tag is linked specifically bind to silicon oxide via the silicon oxide-binding tag. Then, in the dissociating step, specific binding between the silicon oxide-binding tag and silicon oxide is broken with use of arginine.

The dissociating step may be carried out by, for example, bringing a complex (specifically, a complex of the silicon oxide-binding tag and the substance) which is bound to silicon oxide into contact with an eluate containing arginine.

Since specific binding between the silicon oxide-binding tag and silicon oxide is broken with use of arginine in the dissociating step, the eluate should contain only arginine as a dissociating agent for breaking the specific binding between the silicon oxide-binding tag and silicon oxide.

Specifically, the eluate may be a solvent (e.g., water, a Tris-HCl buffer solution, a HEPES buffer solution, or a phosphate buffer solution) in which (i) arginine is contained and (ii) NaCl, KCl, ammonium sulfate, a surfactant (e.g., polyoxyethylene sorbitan monolaurate or Triton X-100 (registered trademark)), acetonitrile, or citric acid is not contained.

The eluate may be a solvent (e.g., water, a Tris-HCl buffer solution, a HEPES buffer solution, or a phosphate buffer solution) in which (i) arginine is contained and (ii) at least one selected from the group consisting of NaCl, KCl, ammonium sulfate, a surfactant (e.g., polyoxyethylene sorbitan monolaurate or Triton X-100 (registered trademark)), acetonitrile, and citric acid is not contained.

The eluate may be a solvent (e.g., water, a Tris-HCl buffer solution, a HEPES buffer solution, or a phosphate buffer solution) in which (i) arginine is contained and (ii) NaCl, KCl, ammonium sulfate, a surfactant (e.g., polyoxyethylene sorbitan monolaurate or Triton X-100 (registered trademark)), acetonitrile, and citric acid are not contained.

The eluate may be a solvent (e.g., water or a Tris-HCl buffer solution) which contains only arginine.

A concentration of arginine contained in the eluate is not particularly limited, but is preferably not less than 0.01 M, more preferably not less than 0.05 M, more preferably not less than 1.0 M, more preferably not less than 1.5 M, and most preferably not less than 2.0 M. Note here that an upper limit of the concentration of arginine is not particularly limited, and may be 10 M, 9.0 M, 8.0 M, 7.0 M, 6.0 M, 5.0 M, 4.0 M, or 3.0 M. This configuration allows binding between the silicon oxide-binding tag and silicon oxide to be efficiently broken.

A pH of the eluate is not particularly limited, but is preferably not less than pH 6.0 and not more than pH 9.0, and more preferably not less than pH 7.0 and not more than pH 8.0. This configuration allows binding between the silicon oxide-binding tag and silicon oxide to be efficiently broken.

The purification method of the present embodiment may include a step other than the dissociating step. For example, breaking binding between the silicon oxide-binding tag and silicon oxide with use of arginine in the dissociating step yields a mixture of a complex to be purified and arginine. As such, the purification method of the present embodiment may include a removing step of removing arginine from the mixture. A specific configuration of the removing step is not limited, but, for example, arginine may be removed from the mixture by dialysis with use of a commercially available dialysis membrane. This configuration allows obtaining a complex with higher purity.

<2. Silicon Oxide-binding Tag>

A silicon oxide-binding tag of the present embodiment has a silicon oxide-binding capacity. In addition to having the binding capacity, the silicon oxide-binding tag of the present embodiment may be such a silicon oxide-binding tag that binding between the silicon oxide-binding tag and silicon oxide is broken with use of arginine.

More specifically, the silicon oxide-binding tag of the present embodiment is a silicon oxide-binding tag containing a polypeptide constituted by not more than seven amino acids, and not less than 3/7 and less than 7/7 of all amino acids constituting the polypeptide may be arginine.

As a size of the silicon oxide-binding tag decreases, a significant change in structure of a desired substance can be prevented more when the silicon oxide-binding tag is linked with the desired substance. In other words, a decrease in size of the silicon oxide-binding tag allows further preventing a desired substance (e.g., a polymer such as a protein) from losing a function (e.g., an enzyme activity) when the silicon oxide-binding tag is linked with the desired substance. Further, a decrease in size of the silicon oxide-binding tag allows a complex of the silicon oxide-binding tag and a desired substance to have a greater solubility in an aqueous solution when the silicon oxide-binding tag is linked with the desired substance. The silicon oxide-binding tag of the present embodiment exhibits these effects to significant degrees, due to being a silicon oxide-binding tag that contains a polypeptide constituted by not more than seven amino acids.

The number of amino acids constituting the polypeptide should be not more than seven, but is more preferably not more than six, more preferably not more than five, and most preferably not more than four. A lower limit of the number of amino acids is not particularly limited, but may be seven, six, five, four, or three.

An amino acid constituting the polypeptide is not limited to a particular kind, but preferably not less than 3/7 and not more than 7/7, more preferably not less than 3/7 and not more than 6/7, more preferably not less than 3/7 and not more than 5/7, more preferably not less than 3/7 and not more than 4/7, and most preferably 3/7, of all amino acids constituting the polypeptide are arginine. This configuration allows the silicon oxide-binding tag to bind to silicon oxide efficiently. Further, the configuration allows binding between the silicon oxide-binding tag and silicon oxide to be efficiently broken by arginine. Meanwhile, in a case where all amino acids constituting the silicon oxide-binding tag are arginine, an efficiency of binding of the silicon oxide-binding tag to silicon oxide tends to decrease.

The polypeptide constituting the silicon oxide-binding tag of the present embodiment may contain, as at least part of the polypeptide, a polypeptide of (c) or (d):

(c) a polypeptide having an amino acid sequence of SEQ ID NO: 3; and (d) a polypeptide having an amino acid sequence of SEQ ID NO: 3 in which one or several amino acids are deleted, substituted, or added, the polypeptide having a silicon oxide-binding capacity.

A polypeptide having amino acids of SEQ ID NO: 3 is a partial peptide of a CotB1 protein derived from *Bacillus cereus* (e.g., *Bacillus cereus* ATCC 14579), which is a prokaryote.

The polypeptide of (d) above is preferably a polypeptide which (i) has an amino acid sequence of SEQ ID NO: 3 in which one or several amino acids other than arginine are deleted, substituted, or added and (ii) has a silicon oxide-binding capacity. This configuration not only allows the silicon oxide-binding tag to bind to silicon oxide efficiently but also allows binding between the silicon oxide-binding tag and silicon oxide to be efficiently broken by arginine.

The term "one or several amino acids are deleted, substituted, or added" in the peptide of (d) above means that a certain number (preferably not more than four, more preferably not more than three, more preferably not more than two, and most preferably not more than one) of amino acids, in which number the amino acids can be deleted, substituted, or added by a known mutant peptide production method such as site-directed mutagenesis, are deleted, substituted, or added.

The peptide of (d) above may be a polypeptide which (i) has an amino acid sequence having a sequence identity of preferably not less than 30%, more preferably not less than 35%, more preferably not less than 40%, more preferably not less than 45%, more preferably not less than 50%, more preferably not less than 60%, more preferably not less than 70%, more preferably not less than 80%, more preferably not less than 90%, more preferably not less than 95%, more preferably not less than 96%, more preferably not less than 97%, more preferably not less than 98%, and most preferably not less than 99% with respect to an amino acid sequence of SEQ ID NO: 3 and (ii) has a silicon oxide-binding capacity.

Examples of preferable mutation encompass substitution, deletion, or addition of an amino acid. Among these examples of mutation, the substitution of an amino acid is particularly preferable.

The substitution of an amino acid is not particularly limited, but may be such substitution in which a given amino acid is substituted with glycine or alanine. More specifically, the substitution of an amino acid may be such substitution in which serine, glycine, alanine, or glutamine is substituted with glycine or alanine. Of course, the present invention is not limited to the substitutions described above.

<3. Kit>

A kit of the present embodiment is a kit for purifying a complex of a silicon oxide-binding tag and a substance, including: a column which contains silicon oxide as a stationary phase for separation; a silicon oxide-binding tag which binds to the silicon oxide; a solution for binding, to which solution no salt is added and which solution is for causing the complex to specifically bind to the silicon oxide; and a solution for dissociation, which solution contains arginine and is for breaking binding between the silicon oxide-binding tag and the silicon oxide.

The column may be any column that includes silicon oxide as a stationary phase for separation, and a specific configuration of the column is not limited. The column may be a commercially available column.

The silicon oxide-binding tag has already been described above, and detailed description thereof will be omitted. The kit of the present embodiment may include the silicon oxide-binding tag itself, or may include a configuration which is capable of producing the silicon oxide-binding tag or a complex of the silicon oxide-binding tag and a substance. For example, the kit of the present embodiment may include a vector for expressing a recombinant protein, into which vector a polynucleotide encoding the silicon oxide-binding tag is inserted. In this case, a user of the kit can insert a polynucleotide encoding a desired protein into the vector so as to use the vector as a vector for expressing a complex.

The solution for binding and the solution for dissociation have already been described above, and descriptions thereof will be omitted.

The present invention may also be configured as follows.

In order to attain the object, a purification method of the present invention is a method for purifying a complex, including a dissociating step of causing a complex of a silicon oxide-binding tag and a substance to be dissociated from silicon oxide to which the complex is specifically bound, the dissociating step being a step of causing arginine to break binding between the silicon oxide-binding tag and the silicon oxide.

The purification method of the present invention is preferably configured such that the substance is a protein.

The purification method of the present invention is preferably configured such that the dissociating step is a step of bringing the complex, which is bound to the silicon oxide, into contact with an eluate containing arginine; and the eluate contains only the arginine as a dissociating agent for breaking specific binding between the silicon oxide-binding tag and silicon oxide.

The purification method of the present invention is preferably configured such that the silicon oxide is contained in *Shirasu*.

The purification method of the present invention is preferably configured such that the silicon oxide-binding tag contains a polypeptide; and not less than 5/14 and less than 7/7 of all amino acids constituting the polypeptide are arginine.

The purification method of the present invention is preferably configured such that the polypeptide has not more than 14 amino acids.

The purification method of the present invention is preferably configured such that the polypeptide includes, as at least part thereof, a polypeptide of (a) or (b):

(a) a polypeptide having an amino acid sequence of SEQ ID NO: 1, 3, 5, 20, or 21; and (b) a polypeptide having an amino acid sequence of SEQ ID NO: 1, 3, 5, 20 or 21 in which one or several amino acids are deleted, substituted, or added, the polypeptide having a silicon oxide-binding capacity.

In order to attain the object, a silicon oxide-binding tag of the present invention is a silicon oxide-binding tag containing a polypeptide having not more than seven amino acids, not less than 3/7 and less than 7/7 of all amino acids constituting the polypeptide being arginine.

The silicon oxide-binding tag of the present invention is preferably configured such that the polypeptide includes, as at least part thereof, a polypeptide of (c) or (d):

(c) a polypeptide having an amino acid sequence of SEQ ID NO: 3; and (d) a polypeptide having an amino acid sequence of SEQ ID NO: 3 in which one or several amino acids are deleted, substituted, or added, the polypeptide having a silicon oxide-binding capacity.

EXAMPLES

1. Production of Plasmid for Expressing Fusion Protein of Tag and GFP

In order to identify a silicon oxide-binding domain in a CotB1 peptide, a plasmid for expressing a fusion protein of (i) a mutant peptide which is obtained by deleting part of a CotB1 peptide having 14 amino acids and (ii) GFP (Green Fluorescent Protein) was produced.

First, with use of, as a template, a plasmid (pET-GFP-CotB1p: Abdelhamid et al., Applied Microbiology and Biotechnology, 98(12), 5677-5684, 2014) expressing a fusion protein (CotB1p-GFP) of a wild CotB1 peptide shown in Table 1 and GFP, an inverse PCR method was performed so as to construct plasmids (pET-GFP-CotB1p (#9), pET-GFP-CotB1p (#10), and pET-GFP-CotB1p (#11)), each for expressing a fusion protein of (i) a corresponding one of three kinds of mutant CotB1 peptides (#9 to #11) shown in Table 1 and (ii) GFP.

Specifically, the termini of a DNA fragment obtained by the inverse PCR method were phosphorylated with use of T4 polynucleotide kinase (Takara Bio), and the DNA fragment thus phosphorylated was circularized with use of Ligation high (TOYOBO). Subsequently, with use of the circularized DNA fragment, a cloning host *Escherichia coli* JM109 was transformed, and *Escherichia coli* into which a desired plasmid had been introduced was selected. Then, the desired plasmid was purified from the *Escherichia coli* in accordance with a known method.

TABLE 1

| CotB1 peptide | | Amino acid sequence or DNA sequence | Binding force ratio | SEQ ID NO |
|---|---|---|---|---|
| Wild | Amino acid | SGRARAQRQSSRGR | 100 | 1 |
| | DNA | TCAGGTCGTGCTCGTGCACAAAGACAAT CAAGTAGAGGAAGA | – | 2 |
| Mutant (#9) | Amino acid | RQSSRGR | 92 | 3 |
| | DNA | AGACAAT CAAGTAGAGGAAGA | – | 4 |
| Mutant (#10) | Amino acid | RAQRQSSRGR | 93 | 5 |
| | DNA | CGTGCACAAAGACAAT CAAGTAGAGGAAGA | – | 6 |
| Mutant (#11) | Amino acid | SGRARAQR | 70 | 7 |
| | DNA | TCAGGTCGTGCTCGTGCACAAAGA | – | 8 |

2. Evaluation of Binding Force of Fusion Protein with Respect to Silicon Oxide

Each plasmid purified in <1> was introduced by a known method into a host for protein expression, *Escherichia coli* Rosetta 2 (DE3)pLysS (Novagen), so that a transformant was obtained.

The transformant was cultured in a 2×YT medium containing 1% glucose at 37° C. until $OD_{600}$ became 0.5. Subsequently, 0.2 mM IPTG (isopropyl β-D-1-thiogalactopyranoside) was added in the medium and cultured at 37° C. for another 4 hours, so that bacterial cells expressing a large amount of a corresponding fusion protein were obtained.

The bacterial cells expressing each fusion protein were suspended in a reaction buffer (25 mM Tris-HCl (pH 8.0), 0.5% (v/v) Tween 20 (registered trademark)), and were disrupted by ultrasonication. A lysate thus obtained was subjected to centrifugal separation (20,000×g, 30 minutes, 4° C.), and a supernatant obtained through the centrifugal separation was collected as a fusion protein extract, which was to be used as an extracted fraction of the bacterial cells.

To 0.1 mL of a reaction buffer containing 10 mg of silicon oxide particles (Silicon dioxide fine powder ca. 0.8 μm, Soekawa Rikagaku), the fusion protein extract, which had been diluted as appropriate, was added and mixed at room temperature for 30 minutes. Subsequently, the silicon oxide particles were precipitated by centrifugal separation (5,000× g, 2 minutes, 25° C.), and a supernatant and a precipitate were collected as a non-binding fraction and a silicon oxide-binding fraction, respectively.

A fluorescence value derived from GFP of each of the samples (the extracted fraction of the bacterial cells and the non-binding fraction) thus obtained was measured, and a difference obtained by subtracting the fluorescence value of the non-binding fraction from the fluorescence value of the extracted fraction of the bacterial cells was used as a fluorescence value of the silicon oxide-binding fraction.

A ratio (the fluorescence value of the silicon oxide-binding fraction/the fluorescence value of the extracted fraction of the bacterial cells) of a fusion protein which bound to silicon oxide among the fusion protein in the extracted fraction of the bacterial cells was used as an index so as to compare binding forces of the respective mutant CotB1 peptides.

Note that a similar test was carried out with respect to (i) a positive control *Escherichia coli* Rosetta 2 (DE3)pLysS (Novagen) into which a plasmid (pET-GFP-CotB1p) for expressing a fusion protein of a wild CotB1 peptide and GFP had been introduced and (ii) a negative control *Escherichia coli* Rosetta 2 (DE3)pLysS (Novagen) into which a plasmid (pET-GFP) for expressing only GFP had been introduced.

Test results are shown in Table 1. The results revealed that each of the mutant CotB1 peptides had a binding force of as high as not less than 70% of a binding force of the wild CotB1 peptide.

The results also revealed that each of the mutant CotB1 peptides (in particular, #9) had a high binding force equivalent to the binding force of the wild CotB1 peptide, in spite of being a small peptide having very few amino acids (seven amino acids).

Each of the mutant CotB1 peptides has a size substantially identical to a His-tag (a tag which has six amino acids and exhibits affinity for $Ni^{2+}$ and the like) which is widely used in purification of a recombinant protein. That is, the mutant CotB1 peptides are very small as a tag to be fused to a desired protein. It is therefore assumed that when fused to a desired protein, the mutant CotB1 peptides have little influence on the desired protein. Note that Table 2 shows typical well-known tags.

TABLE 2

| Tag name | Size (aa) | Object to which the tag binds |
|---|---|---|
| Si-tag | 273 | $SiO_2$ |
| MBP | 396 | Amylose |
| His-tag | 6 | Ni-NTA/Talon |
| GST | 218 | Glutathione-Sepharose |
| CBP | 28 | Calmodulin Affinity |
| Strep II | 8 | Strep-Tactin-Sepharose |
| FLAG | 8 | Anti-FLAG M2 MAb agarose |
| HPC | 12 | Anti-Protein C MAb matrix |
| CYD | 5 | InaD |

Note:
Modified from Lichty et al. Protein Expr. Purif. 41, 98-105 (2005)

3. Identification of Amino Acid in Tag which Amino Acid is Important for Binding Force of Tag The mutant CotB1 peptide (#9) was analyzed as to which one of the seven amino acids was important for binding to silicon oxide.

First, with use of, as a template, a plasmid (pET-GFP-CotB1p (#9)) expressing a fusion protein of the mutant CotB1 peptide (#9) and GFP, an inverse PCR method was performed so as to construct a plasmid (pET-GFP-CotB1p (#12), pET-GFP-CotB1p (#13), pET-GFP-CotB1p (#14), pET-GFP-CotB1p (#15), pET-GFP-CotB1p (#16), pET-GFP-CotB1p (#17), pET-GFP-CotB1p (#18), or pET-GFP-($R_9$-tag)) for expressing a fusion protein of (i) each of seven kinds of mutant CotB1 peptides (#12 to #18) shown in Table 3 or an $R_9$-tag and (ii) GFP. Note that the seven kinds of mutant CotB1 peptides shown in Table 3 are peptides obtained by substituting, with alanine, the respective seven amino acids constituting the mutant CotB1 peptide (#9).

Specifically, the termini of a DNA fragment obtained by the inverse PCR method were phosphorylated with use of T4 polynucleotide kinase (Takara Bio), and the DNA fragment thus phosphorylated was circularized with use of Ligation high (TOYOBO). Subsequently, the circularized DNA fragment was transformed into a cloning host Escherichia coli JM109, and Escherichia coli into which a desired plasmid had been introduced was selected. Then, the desired plasmid was purified from the Escherichia coli in accordance with a known method.

Evaluation of a binding force of each fusion protein was made in accordance with the method described in <2>. Expression of the fusion protein of the $R_9$-tag and GFP was conducted in accordance with a method described in a document by Taniguchi et al. (Koji Taniguchi et al., Biotechnology and Bioengineering Vol. 96, No. 6, April 15, p 1023-1029, 2007).

Test results are shown in Table 3.

Analysis revealed that a binding force significantly decreased in a case where any one of the three arginines in the seven amino acids constituting the mutant CotB1 peptide (#9) was substituted with alanine (see #12, #16, and #18 of Table 3).

Meanwhile, in a case where an amino acid (e.g., glutamine, serine, and glycine) other than arginine was substituted with alanine, decrease in binding force was hardly observed.

Further, the fusion protein of the $R_9$-tag and GFP, which was used as a control, hardly bound to silicon oxide under the conditions of the test. It has been reported that an $R_9$-tag binds to silicon oxide (S. M. Fuchs & R. T. Raines (2005) Polyarginine as a multifunctional fusion tag, Protein Sci. 14, 1538-1544). It is assumed that under the conditions of the test, binding to silicon oxide was blocked by a surfactant (specifically, polyoxyethylene sorbitan monolaurate (more specifically, 0.5% (v/v) Tween 20 (registered trademark))) contained in the reaction buffer.

From these results, it is assumed that, although arginine is the most important for binding between the mutant CotB1 peptide (#9) and silicon oxide, amino acids other than arginine also made a great contribution, in view of a low binding force of the $R_9$-tag which was constituted solely of arginine. However, given that very little decrease in binding force was observed in cases where an amino acid other than arginine was substituted with alanine, it is assumed that the amino acids other than arginine function as a spacer between arginines.

TABLE 3

| | Amino acid sequence | Binding force ratio | SEQ ID NO. |
|---|---|---|---|
| Mutant CotB1 peptide (#9) | RQSSRGR | 100 | 3 |
| Mutant CotB1 peptide (#12) | AQSSRGR | 20 | 9 |
| Mutant CotB1 peptide (#13) | RASSRGR | 89 | 10 |
| Mutant CotB1 peptide (#14) | RQASRGR | 91 | 11 |
| Mutant CotB1 peptide (#15) | RQSARGR | 88 | 12 |
| Mutant CotB1 peptide (#16) | RQSSAGR | 25 | 13 |
| Mutant CotB1 peptide (#17) | RQSSRAR | 95 | 14 |
| Mutant CotB1 peptide (#18) | RQSSRGA | 12 | 15 |
| $R_9$-tag | RRRRRRRRR | 3 | 16 |

<4. Comparison Between Binding Force of Mutant CotB1 Peptide with Respect to Silicon Oxide and Binding Force of $R_9$-Tag with Respect to Silicon Oxide>

In accordance with a method described above, (i) Escherichia coli Rosetta 2 (DE3)pLysS (Novagen) into which pET-GFP-CotB1p (#9) had been introduced and (ii) Escherichia coli Rosetta 2 (DE3)pLysS (Novagen) into which pET-GFP—($R_9$-tag) had been introduced were produced.

A desired fusion protein was expressed in each Escherichia coli. Then, each Escherichia coli was suspended in 25 mM Tris-HCl buffer solutions (pH 8.0) containing Tween 20 (registered trademark) at respective different concentrations (0% (v/v), 0.05% (v/v), 0.1% (v/v), or 0.5% (v/v)), and extracted fractions of bacterial cells were prepared in accordance with the method described in <2>.

To 1 mL of each of the extracted fractions of bacterial cells, 25 mg of silicon oxide particles (Silicon dioxide fine powder ca. 0.8 μm, Soekawa Rikagaku) were added and mixed at room temperature for 15 minutes. Subsequently, with use of a Tris-HCl buffer solution having the same composition as that of the Tris-HCl buffer solution in which the bacterial cells had been suspended, the silicon oxide particles were washed five times. The silicon oxide particles thus washed were collected by centrifugal separation. Subsequently, the silicon oxide particles were suspended in a sample buffer for SDS-PAGE and heated at 95° C. for five minutes, so that a fusion protein which had bound to a surface of the silicon oxide particles was dissociated from the silicon oxide particles. Then, the sample buffer containing the dissociated fusion protein was subjected to SDS-PAGE.

Test results are shown in FIG. 1. Note that in FIG. 1, "M" indicates a molecular weight marker, "S" indicates a test result of one of the extracted fractions of bacterial cells, lanes "1" and "2" each show a test result of a Tris-HCl buffer solution containing no Tween 20 (registered trademark), a lane "3" indicates a test result of a Tris-HCl buffer solution containing 0.05% (v/v) Tween 20 (registered trademark), a lane "4" indicates a test result of a Tris-HCl buffer solution containing 0.1% (v/v) Tween 20 (registered trademark), and a lane "5" indicates a test result of a Tris-HCl buffer solution containing 0.5% (v/v) Tween 20 (registered trademark).

As is clear from FIG. 1, the fusion protein of the mutant CotB1 peptide (#9) and GFP bound to silicon oxide regardless of the presence/absence of a surfactant Tween 20 (registered trademark), whereas the fusion protein of the $R_9$-tag and GFP was not able to bind to silicon oxide in the presence of Tween 20 (registered trademark).

Tween 20 (registered trademark) is widely used in order to prevent a protein other than a desired protein from being adsorbed nonspecifically onto, for example, a column for purification, in other words, in order to enhance the purity of a desired protein which is purified.

Due to being capable of binding to silicon oxide even in the presence of Tween 20 (registered trademark), the mutant CotB1 peptide is more versatile than the $R_9$-tag and allows a desired protein to be fixed and purified with higher purity.

<5. Specific Elution of Fusion Protein from Silicon Oxide—19>

In accordance with a method described above, *Escherichia coli* Rosetta 2 (DE3)pLysS (Novagen) into which pET-GFP-CotB1p (#9) had been introduced was produced.

A desired fusion protein was expressed in the *Escherichia coli* above. Then, the *Escherichia coli* was suspended in 25 mM Tris-HCl buffer solution (pH 8.5) containing 0.05% (v/v) Tween 20 (registered trademark), and an extracted fraction of bacterial cells was prepared in accordance with the method described in <2>.

To 1 mL of the extracted fraction of the bacterial cells, 25 mg of silicon oxide particles (Silicon dioxide fine powder ca. 0.8 μm, Soekawa Rikagaku) were added and mixed at room temperature for 15 minutes. Subsequently, with use of a Tris-HCl buffer solution having the same composition as that of the Tris-HCl buffer solution in which the bacterial cells had been suspended, the silicon oxide particles were washed four times. The silicon oxide particles thus washed were collected by centrifugal separation.

The silicon oxide particles were suspended in 25 mM Tris-HCl buffer solution (pH 8.0) containing 0.2 M of arginine. Subsequently, the silicon oxide particles were precipitated by centrifugal separation, and a supernatant was collected and subjected to SDS-PAGE. An image of a gel stained with Coomassie brilliant blue R-250 was captured, and a purity and yield of the desired fusion protein were analyzed with image analysis software ImageJ.

Figure 2:
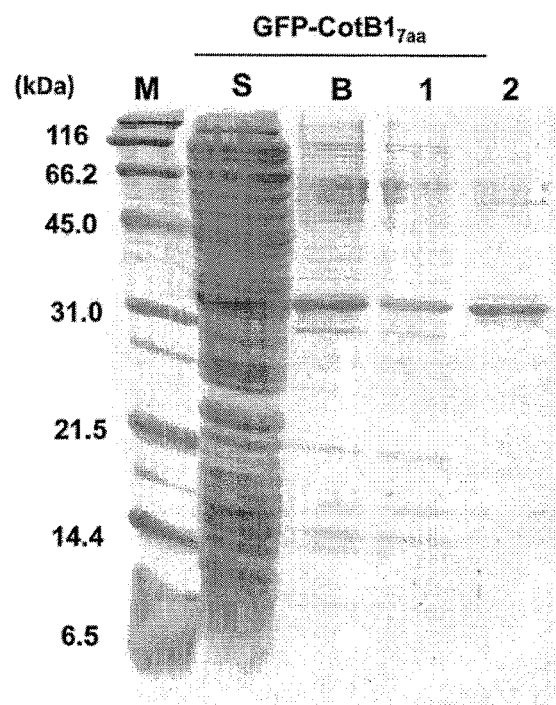
FIG. 2 is an image of a gel in SDS-PAGE, the image showing results of a test in an example of the present invention.

Test results are shown in FIG. 2. Note that in FIG. 2, "M" indicates a molecular weight marker, "S" indicates a test result of the extracted fraction of the bacterial cells, "B" indicates a test result of a protein which was bound to silicon oxide particles after four times of washing, a lane "1" indicates a test result of a protein which was bound to silicon oxide particles even after elution caused by arginine, and a lane "2" indicates a test result of a protein which was dissociated from silicon oxide as a result of the elution by arginine.

As is clear from FIG. 2, it was revealed that the desired fusion protein could be specifically dissociated from silicon oxide with use of arginine. Note that in the case of using arginine, the desired fusion protein was purified with a purity of 90% and a yield of 70%.

6. Specific Elution of Fusion Protein from Silicon Oxide—2

With respect to a Si-tag (amino acid sequence: SEQ ID NO: 18, DNA sequence: SEQ ID NO: 19), an $R_9$-tag (amino acid sequence: SEQ ID NO: 16, DNA sequence: SEQ ID NO: 17), and a partial peptide (TAT-tag, amino acid sequence: SEQ ID NO: 20) of a TAT protein, confirmation was made as to whether or not elution by arginine was possible.

<6-1. Si-tag>

To 25 mM Tris-HCl buffer solution (pH 8.0) containing a protein A (Si-tag fusion protein A; see a document by Ikeda et al. (Analytical Biochemistry, Vol. 385, p 132-137 (2009)) as for expression and purification methods for the Si-tag fusion protein A), which is an antibody protein to which an Si-tag is fused, 5 mg of silicon oxide particles (Silicon dioxide fine powder ca. 0.8 μm, Soekawa Rikagaku) were added and mixed for 15 minutes, so that the Si-tag fusion protein A was adsorbed onto the silicon oxide particles. The silicon oxide particles were washed with 25 mM Tris-HCl buffer solution (pH 8.0) three times, and then the silicon oxide particles thus washed were collected by centrifugal separation.

The silicon oxide particles were suspended in 25 mM Tris-HCl buffer solution (pH 8.0) containing 1 M or 2M of arginine. Subsequently, the silicon oxide particles were precipitated by centrifugal separation, and a supernatant was collected and subjected to SDS-PAGE. A purity and yield of the desired fusion protein were analyzed in accordance with the method described in <5>.

Figure 3:
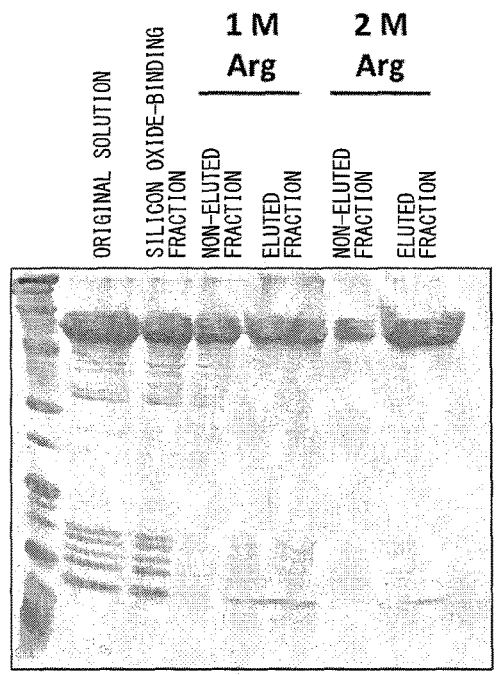
FIG. 3 is an image of a gel in SDS-PAGE, the image showing results of a test in an example of the present invention.

Test results are shown in FIG. 3. As indicated by FIG. 3, it was revealed that the desired fusion protein could be dissociated from silicon oxide with use of arginine. Note that in a case where 1 M of arginine was used, a recovery rate of the desired fusion protein was 60%, and in a case where 2 M of arginine was used, a recovery rate of the desired fusion protein was 85%.

<6-2. $R_9$-Tag>

To 25 mM Tris-HCl buffer solution (pH 8.0) containing (i) 50 mM NaCl and (ii) a fusion protein (see a document by Taniguchi et al. (Koji Taniguchi et al., Biotechnology and Bioengineering Vol. 96, No. 6, April 15, p 1023-1029, 2007) as for expression and purification methods for the fusion protein) of an R9-tag and GFP, 5 mg of silicon oxide particles (Silicon dioxide fine powder ca. 0.8 μm, Soekawa Rikagaku) were added and mixed for 15 minutes, so that the fusion protein of the R9-tag and GFP was adsorbed onto the silicon oxide particles. The silicon oxide particles were washed with 25 mM Tris-HCl buffer solution (pH 8.0) three times, and then the silicon oxide particles thus washed were collected by centrifugal separation.

The silicon oxide particles were suspended in 25 mM Tris-HCl buffer solution (pH 8.0) containing 1 M of arginine. Subsequently, the silicon oxide particles were precipitated by centrifugal separation, and a supernatant was collected and subjected to SDS-PAGE.

Figure 4:
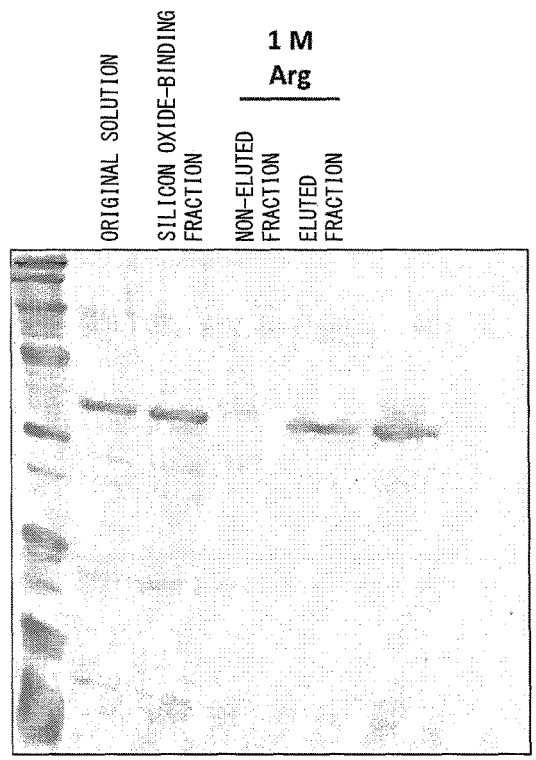
FIG. 4 is an image of a gel in SDS-PAGE, the image showing results of a test in an example of the present invention.

Test results are shown in FIG. 4. As shown in FIG. 4, approximately 100% of the fusion protein of the R9-tag and GFP, which had bound to silicon oxide, was eluted by 1 M of the arginine solution. This shows that elution by arginine is a technique which can be utilized also with respect to various silicon oxide-binding proteins and silicon oxide-binding peptides.

<6-3. Tat-Tag>

A plasmid for expressing a fusion protein of a TAT-tag and GFP was produced.

Specifically, DNA encoding a fusion protein obtained by fusing GFP to the C-terminus of a partial peptide (SEQ ID NO: 20) of a TAT protein was synthesized. Note that an NdeI recognition sequence and an EcoRI recognition sequence were fused to the 5'-terminus and the 3'-terminus, respectively, of the DNA.

The synthesized DNA was digested with use of a restriction enzyme NdeI and a restriction enzyme EcoRI. Then, a digest thus obtained and a pET-47b plasmid (Novagen), which had been digested similarly with use of the restriction enzyme NdeI and the restriction enzyme EcoRI, were subjected to ligation at 16° C. for two hours with use of Ligation High (TOYOBO). Subsequently, with use of a product of the ligation, a cloning host *Escherichia coli* JM109 was transformed, and *Escherichia coli* into which a desired plasmid (pET-TAT-GFP) had been introduced was selected. Then, the desired plasmid was purified from the *Escherichia coli* in accordance with a known method.

In accordance with a method described above, *Escherichia coli* Rosetta 2 (DE3)pLysS (Novagen) into which pET-TAT-GFP had been introduced was produced.

A desired fusion protein was expressed in the *Escherichia coli* above. Then, the *Escherichia coli* was suspended in 25 mM Tris-HCl buffer solution (pH 8.0), and an extracted fraction of bacterial cells was prepared in accordance with the method described in <2>. To 1 mL of the extracted fraction of the bacterial cells, 100 mg of silicon oxide particles (Silicon dioxide fine powder ca. 0.8 μm, Soekawa Rikagaku) were added and mixed at room temperature for 15 minutes. Subsequently, with use of a Tris-HCl buffer solution having the same composition as that of the Tris-HCl buffer solution in which the bacterial cells had been suspended, the silicon oxide particles were washed four times. The silicon oxide particles thus washed were collected by centrifugal separation.

The silicon oxide particles were suspended in 25 mM Tris-HCl buffer solution (pH 8.0) containing 1.0 M of arginine. Subsequently, the silicon oxide particles were precipitated by centrifugal separation, and a supernatant was collected and subjected to SDS-PAGE. Purity and yield were analyzed in accordance with the method described in <5>.

Figure 6:
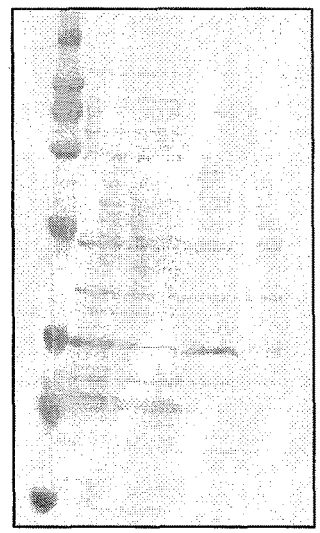
FIG. 6 is an image of a gel in SDS-PAGE, the image showing results of a test in an example of the present invention.

Test results are shown in FIG. 6. Note that in FIG. 6, "M" indicates a molecular weight marker, "S" indicates a test result of the extracted fraction of the bacterial cells, and a lane "1" indicates a test result of a protein which was dissociated from silicon oxide as a result of elution by arginine.

As is clear from FIG. 6, it was revealed that the desired fusion protein could be dissociated specifically from silicon oxide with use of arginine. Note that in the case of using arginine, the desired fusion protein was purified with a purity of 80% and a yield of 70%. This shows that elution by arginine is a technique which can be utilized also with respect to various silicon oxide-binding proteins and silicon oxide-binding peptides.

<7. Specific Elution of Fusion Protein from Silicon Oxide (Shirasu Particles)—3>

In accordance with a method described above, *Escherichia coli* Rosetta 2 (DE3)pLysS (Novagen) into which pET-GFP-CotB1p (#9) had been introduced was produced.

A desired fusion protein was expressed in the *Escherichia coli* above. Then, the *Escherichia coli* was suspended in 25 mM Tris-HCl buffer solution (pH 8.0) containing 1% (v/v) Tween 20 (registered trademark), and a extracted fraction of bacterial cells was prepared in accordance with the method described in <2>.

To 1 mL of the extracted fraction of the bacterial cells, 10 mg of Shirasu particles (yielded in Kagoshima prefecture, Japan), which are a pyroclastic flow deposit containing silicon oxide as a main component, were added and mixed at room temperature for five seconds. Subsequently, with use of a Tris-HCl buffer solution having the same composition as that of the Tris-HCl buffer solution in which the bacterial cells had been suspended, the silicon oxide particles were washed three times. The silicon oxide particles thus washed were collected by centrifugal separation.

The silicon oxide particles were suspended in 25 mM Tris-HCl buffer solution (pH 8.0) containing 0.3 M of arginine. Subsequently, the *Shirasu* particles were precipitated by centrifugal separation, and a supernatant was collected and subjected to SDS-PAGE. Purity and yield were analyzed in accordance with the method described in <5>.

Figure 5:
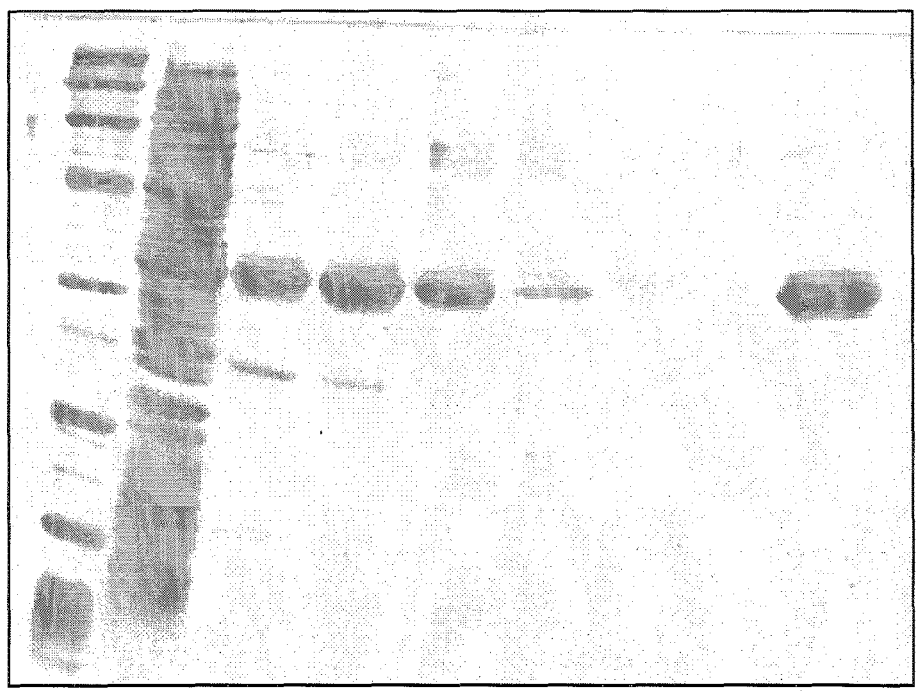
FIG. 5 is an image of a gel in SDS-PAGE, the image showing results of a test in an example of the present invention.

Test results are shown in FIG. 5. Note that in FIG. 5, "M" indicates a molecular weight marker, "S" indicates a test result of the extracted fraction of the bacterial cells, a lane "1" indicates a test result of a protein which was dissociated from the *Shirasu* particles as a result of elution by arginine.

As is clear from FIG. 5, it was revealed that the desired fusion protein could be dissociated specifically from the *Shirasu* particles with use of arginine. Note that in the case of using arginine, the desired fusion protein was purified with a purity of 95% and a yield of 80%.

<7. Purification of mCherry to which CotB1p Peptide (#9) was Fused>

A plasmid for expressing a fusion protein of a CotB1p peptide (#9) and a fluorescent protein mCherry (SEQ ID NO: 22) was produced.

Specifically, first, with use of, as a template, a plasmid (pET-CotB1p-SC: Abdelhamid et al., Applied Microbiology and Biotechnology, 98(12), 5677-5684, 2014) expressing a fusion protein of (i) a wild CotB1 peptide, (ii) SUMO, and (iii) mCherry (CotB1p-GFP), an inverse PCR method was performed so as to construct a plasmid in which a region encoding SUMO had been eliminated. With use of the plasmid thus obtained, an inverse PCR method was performed again so as to delete part of the region of wild CotB1, so that a desired plasmid (pET-CotB1p (#9)-mCherry) was constructed.

In accordance with a method described above, *Escherichia coli* Rosetta 2 (DE3)pLysS (Novagen) into which pET-CotB1p (#9)-mCherry had been introduced was produced.

A desired fusion protein was expressed in the *Escherichia coli* above. Then, the *Escherichia coli* was suspended in 25 mM Tris-HCl buffer solution (pH 8.0) containing 0.5% (v/v) Tween 20 (registered trademark), and an extracted fraction of bacterial cells was prepared in accordance with the method described in <2>.

To 2 mL of the extracted fraction of the bacterial cells, 0.4 g of silicon oxide particles (Silicon dioxide fine powder ca. 0.8 μm, Soekawa Rikagaku) were added and mixed at room temperature for five minutes. Subsequently, with use of a Tris-HCl buffer solution having the same composition as that of the Tris-HCl buffer solution in which the bacterial cells had been suspended, the silicon oxide particles were washed three times. The silicon oxide particles thus washed were collected by centrifugal separation.

The silicon oxide particles were suspended in 25 mM Tris-HCl buffer solution (pH 8.0) containing 0.5 M of arginine. Subsequently, the silicon oxide particles were precipitated by centrifugal separation, and a supernatant was collected and subjected to SDS-PAGE. Purity and yield were analyzed in accordance with the method described in <5>.

Figure 7:
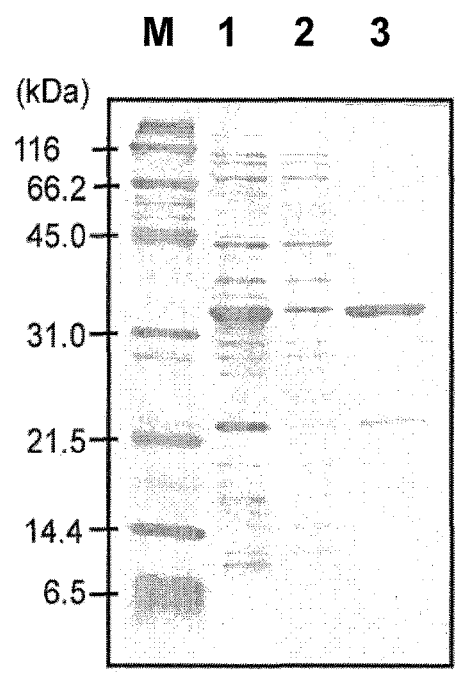
FIG. 7 is an image of a gel in SDS-PAGE, the image showing results of a test in an example of the present invention.

Test results are shown in FIG. 7. Note that in FIG. 7, "M" indicates a molecular weight marker, a lane "1" indicates a test result of the extracted fraction of the bacterial cells, a lane "2" indicates a test result of a protein which was remaining in the supernatant after the extracted fraction of the bacterial cells had been mixed with the silicon oxide particles, and a lane "3" indicates a test result of a protein which was dissociated from silicon oxide as a result of elution by arginine.

As is clear from FIG. 7, it was revealed that the desired fusion protein could be dissociated specifically from silicon oxide with use of arginine. Note that in the case of using arginine, the desired fusion protein was purified with a purity of 89% and a yield of 88%.

<8. Purification of Fusion Protein of CotB1p Peptide (#9) and GFP with Use of Spin Column Including Silica Membrane>

In accordance with a method described above, *Escherichia coli* Rosetta 2 (DE3)pLysS (Novagen) into which pET-GFP-CotB1p (#9) had been introduced was produced.

A desired fusion protein was expressed in the *Escherichia coli* above. Subsequently, the *Escherichia coli* (having a wet weight of approximately 10 mg) was suspended in 500 µL of 25 mM Tris-HCl buffer solution (pH 8.0), and an extracted fraction of bacterial cells was prepared in accordance with the method described in <2>.

To a spin column including a silica membrane which was an accessory of the Wizard SV Gel and PCR Clean-Up System produced by Qiagen, 500 µL of the extracted fraction of the bacterial cells was added, and was left to stand at room temperature for one minute. Subsequently, the spin column was subjected to centrifugal separation (16,000×g, one minute, 4° C.) so as to cause the extracted fraction of the bacterial cells to pass through the silica membrane. To the spin column, 500 µL of 25 mM Tris-HCl buffer solution (pH 8.0) containing 0.5% (v/v) Tween 20 (registered trademark) was added, and the spin column was similarly subjected to centrifugal separation, so that the silica membrane was washed. The washing was further repeated twice, and then the spin column was transferred into a new 1.5 mL microtube. To the spin column, 1 mL of 25 mM Tris-HCl buffer solution (pH 8.0) containing 0.5 M of arginine was added, and the spin column was similarly subjected to centrifugal separation. Then, a solution which had passed through the silica membrane was collected and subjected to SDS-PAGE. Purity and yield were analyzed in accordance with a method described in <5>.

Figure 8:
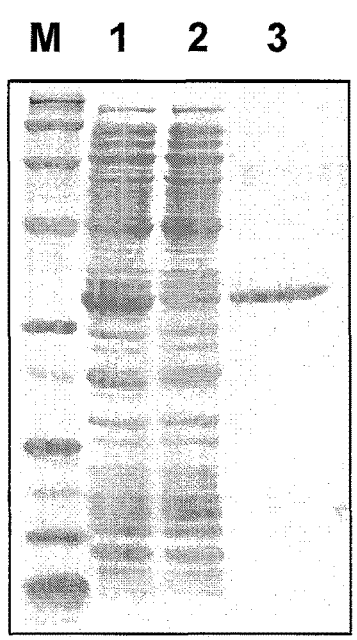
FIG. 8 is an image of a gel in SDS-PAGE, the image showing results of a test in an example of the present invention.

Test results are shown in FIG. 8. Note that in FIG. 8, "M" indicates a molecular weight marker, a lane "1" indicates a test result of the extracted fraction of the bacterial cells, a lane "2" indicates a test result of the extracted fraction of bacterial cells which extracted fraction passed through the silica membrane, and a lane "3" indicates a test result of a protein which was dissociated from the silica membrane as a result of elution by arginine.

As is clear from FIG. 8, it was revealed that with use of the spin column including the silica membrane, (i) the desired fusion protein could be adsorbed onto the silica membrane by centrifugal separation and (ii) the desired fusion protein could be dissociated from the silica membrane using the arginine solution. Note that in the case of using the spin column including the silica membrane, the desired fusion protein was purified with a purity of 89% and a yield of 88%.

<9. Consideration of Condition of Binding of Fusion Protein of CotB1p Peptide (#9) and GFP to Silicon Oxide Particles>

In accordance with a method described above, *Escherichia coli* Rosetta 2 (DE3)pLysS (Novagen) into which pET-GFP-CotB1p (#9) had been introduced was produced.

A desired fusion protein was expressed in the *Escherichia coli* above. Subsequently, the *Escherichia coli* was suspended in (i) 25 mM Tris-HCl buffer solution (pH 8.0) containing 0.5% (v/v) Tween 20 (registered trademark) or (ii) 25 mM Tris-HCl buffer solution (pH 8.0) containing (a) 0.5% (v/v) Tween 20 (registered trademark) and (b) 0.15 M or 0.5 M of NaCl, and an extracted fraction of bacterial cells was prepared in accordance with the method described in <2>.

To 2 mL of the extracted fraction of the bacterial cells, 0.4 g of silicon oxide particles (Silicon dioxide fine powder ca. 0.8 µm, Soekawa Rikagaku) were added and mixed at room temperature for five minutes. Subsequently, with use of a Tris-HCl buffer solution having the same composition as that of the Tris-HCl buffer solution in which the bacterial cells had been suspended, the silicon oxide particles were washed three times. The silicon oxide particles thus washed were collected by centrifugal separation. Subsequently, the silicon oxide particles were suspended in a sample buffer for SDS-PAGE and heated at 95° C. for five minutes, so that a fusion protein which had bound to a surface of the silicon oxide particles was dissociated from the silicon oxide particles. Then, the sample buffer containing the dissociated fusion protein was subjected to SDS-PAGE.

Figure 9:
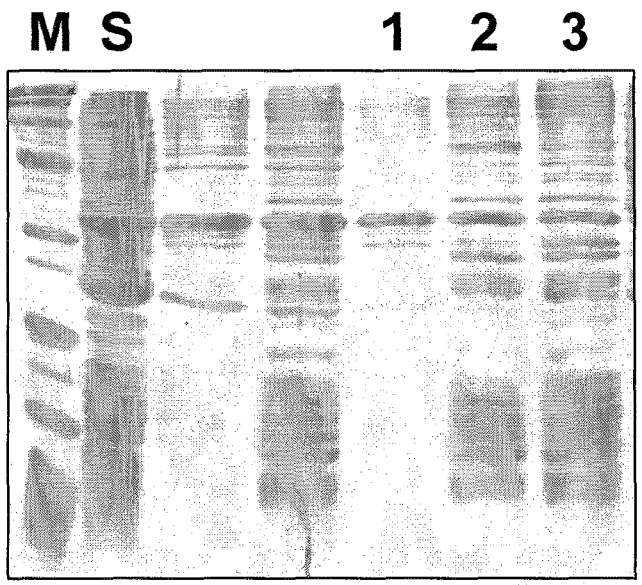
FIG. 9 is an image of a gel in SDS-PAGE, the image showing results of a test in an example of the present invention.

Test results are shown in FIG. 9. Note that in FIG. 9, "M" indicates a molecular weight marker, a lane "S" indicates a test result of the extracted fraction of the bacterial cells, a lane "1" indicates a test result of a protein purified in a case where 25 mM Tris-HCl buffer solution (pH 8.0) containing 0.5% (v/v) Tween 20 (registered trademark) was used, a lane "2" indicates a test result of a protein purified in a case where 25 mM Tris-HCl buffer solution (pH 8.0) containing (i) 0.15 M of NaCl and (ii) 0.5% (v/v) Tween 20 (registered trademark) was used, and a lane "3" indicates a test result of a protein purified in a case where 25 mM Tris-HCl buffer solution (pH 8.0) containing (i) 0.5 M of NaCl and (ii) 0.5% (v/v) Tween 20 (registered trademark) was used.

As is clear from FIG. 9, it was revealed that in a case where a buffer solution containing NaCl was used, many proteins derived from *Escherichia coli* also bound to silicon oxide particles, whereas in a case where a buffer solution containing no NaCl was used, it was possible to cause the desired fusion protein to bind specifically to silicon oxide particles.

<10. Comparison of how Fusion of CotB1p Peptide (Wild) to Protein and Fusion of CotB1p Peptide (#9) to Protein Influence Respective Proteins>

A plasmid for expressing a fusion protein obtained by fusion of a CotB1p peptide (wild) or a CotB1p peptide (#9) to dihydrofolate reductase (DHFR) was produced.

Specifically, DNA encoding a fusion protein obtained by fusing the CotB1p peptide (wild) or the CotB1p peptide (#9) to the carboxyl-terminus of DHFR (SEQ ID NO: 23) of the *B. subtilis* 168 strain was synthesized. Note that a SacII recognition sequence and an XhoI recognition sequence were added to the 5'-terminus and the 3'-terminus, respectively, of the DNA.

The synthesized DNA was digested with use of a restriction enzyme SacII and a restriction enzyme XhoI. Then, a digest thus obtained and a pET-47b plasmid (Novagen), which had been digested similarly with use of the restriction enzyme SacII and the restriction enzyme XhoI, were subjected to ligation at 16° C. for two hours with use of Ligation High (TOYOBO). Subsequently, with use of a product of the ligation, a cloning host *Escherichia coli* JM109 was transformed, and *Escherichia coli* into which a desired plasmid (pET-DHFR-GFP) had been introduced was selected. Then, the desired plasmid was purified from the *Escherichia coli* in accordance with a known method.

In accordance with a method described above, *Escherichia coli* Rosetta 2 (DE3)pLysS (Novagen) into which pET-DHFR-GFP had been introduced was produced.

A desired fusion protein was expressed in the *Escherichia coli* above. Then, the *Escherichia coli* was suspended in 25 mM Tris-HCl buffer solution (pH 8.0) containing 0.5% (v/v) Tween 20 (registered trademark), and an extracted fraction of bacterial cells was prepared in accordance with the method described in <2>.

To 2 mL of the extracted fraction of the bacterial cells, 0.4 g of silicon oxide particles (Silicon dioxide fine powder ca. 0.8 μm, Soekawa Rikagaku) were added and mixed at room temperature for five minutes. Subsequently, with use of a Tris-HCl buffer solution having the same composition as that of the Tris-HCl buffer solution in which the bacterial cells had been suspended, the silicon oxide particles were washed three times. The silicon oxide particles thus washed were collected by centrifugal separation.

The silicon oxide particles were suspended in 25 mM Tris-HCl buffer solution (pH 8.0) containing 0.5 M of arginine. Subsequently, the silicon oxide particles were precipitated by centrifugal separation, and a supernatant was collected. The elution by arginine was performed twice in total. Then, the supernatant was subjected to SDS-PAGE. Purity and yield were analyzed in accordance with the method described in <5>.

Figure 10:
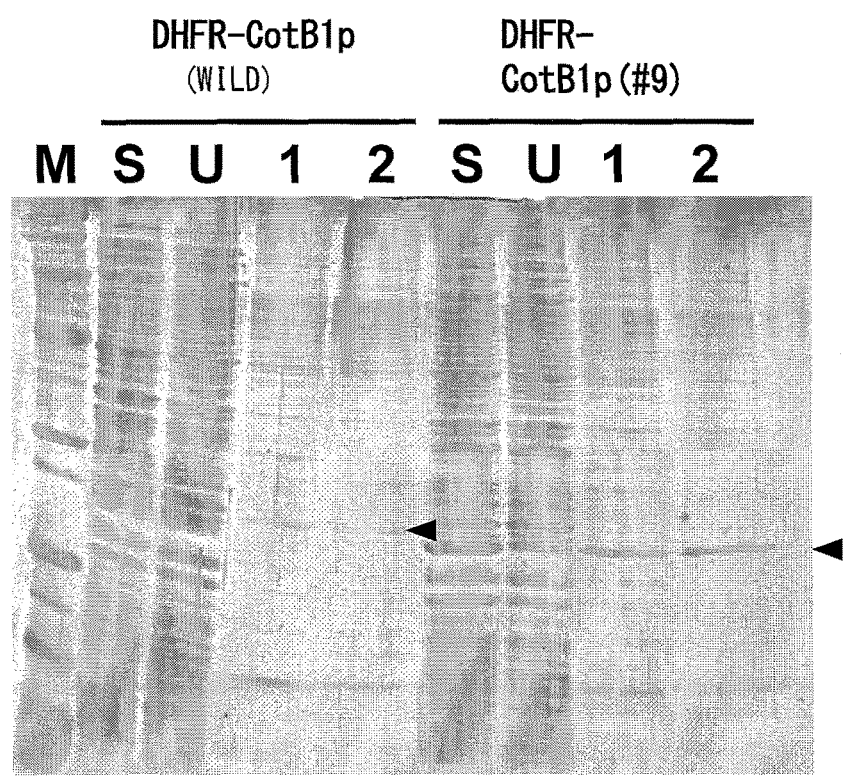
FIG. 10 is an image of a gel in SDS-PAGE, the image showing results of a test in an example of the present invention.

Test results are shown in FIG. 10. Note that in FIG. 10, "M" indicates a molecular weight marker, "S" indicates a test result of the extracted fraction of the bacterial cells, "U" indicates a test result of a protein (non-binding fraction) which did not bind to the silicon oxide particles when the extracted fraction of the bacterial cells and the silicon oxide particles were mixed with each other, and each of lanes "1" and "2" indicates a test result of a protein which was dissociated from silicon oxide as a result of elution by arginine.

As is clear from FIG. 10, in a case where the CotB1p peptide (#9) was fused to DHFR, the fusion protein was expressed as a soluble protein and could be collected with high purity and high yield. Meanwhile, in a case where the CotB1p peptide (wild) was fused to DHFR, expression of the fusion protein as a soluble protein was difficult as compared with the case in which the CotB1p peptide (#9) was fused to DHFR.

In other words, it was revealed that the smaller the peptide was (e.g., the CotB1p peptide (#9)), the more soluble the fusion protein was. Note that in the case where the CotB1p peptide (#9) was fused to DHFR, approximately 7% of all proteins contained in the extracted fraction of the bacterial cells were desired fusion proteins, whereas in the case where the CotB1p peptide (wild) was fused to DHFR, less than 1% of all the proteins contained in the extracted fraction of the bacterial cells were desired fusion proteins.

INDUSTRIAL APPLICABILITY

The present invention is applicable to purification of various substances.

What is claimed is:

1. A method for purifying a complex, comprising:
a binding step of causing a complex of a silicon oxide-binding tag and a substance to specifically bind to silicon oxide in a solution for binding, to which solution no salt is added; and
a dissociating step of dissociating the complex from the silicon oxide,
the dissociating step being a step of causing arginine to break binding between the silicon oxide-binding tag and the silicon oxide.

2. The method as set forth in claim 1, wherein the solution for binding is:
a solution consisting of a pH buffer solution and a solvent; or
a solution consisting of a pH buffer solution, a surfactant, and a solvent.

3. The method as set forth in claim 1, wherein the substance is a protein.

4. The method as set forth in claim 1, wherein:
the dissociating step is a step of bringing the complex, which is bound to the silicon oxide, into contact with an eluate containing arginine; and
the eluate contains only the arginine as a dissociating agent for breaking specific binding between the silicon oxide-binding tag and the silicon oxide.

5. The method as set forth in claim 1, wherein the silicon oxide is contained in Shirasu.

6. The method as set forth in claim1, wherein:
the silicon oxide-binding tag contains a polypeptide; and
not less than 5/14 and less than 7/7 of all amino acids constituting the polypeptide are arginine.

7. The method as set forth in claim 6, wherein the polypeptide has not more than 14 amino acids.

8. The method as set forth in claim 6, wherein the polypeptide includes, as at least part thereof, a polypeptide of (a) or (b):
(a) a polypeptide having an amino acid sequence of SEQ ID NO: 1, 3, 5, 20, or 21; and
(b) a polypeptide having an amino acid sequence of SEQ ID NO: 1, 3, 5, 20 or 21 in which one or several amino acids are deleted, substituted, or added, the polypeptide having a silicon oxide-binding capacity.

9. A silicon oxide-binding tag comprising a polypeptide having not more than seven amino acids,
not less than 3/7 and less than 7/7 of all amino acids constituting the polypeptide being arginine,
wherein the polypeptide comprises (c) or (d):
(c) a polypeptide having an amino acid sequence of SEQ ID NO: 3; and
(d) a polypeptide having an amino acid sequence of SEQ ID NO: 3 in which not more than four amino acids are deleted or substituted, wherein the polypeptide has a silicon oxide-binding capacity.

10. A kit for purifying a complex of a silicon oxide-binding tag and a substance, comprising:
a column which contains silicon oxide as a stationary phase for separation;
a silicon oxide-binding tag which binds to the silicon oxide;
a solution for binding, to which solution no salt is added and which solution is for causing the complex to specifically bind to the silicon oxide; and
a solution for dissociation, which solution contains arginine and is for breaking binding between the silicon oxide-binding tag and the silicon oxide.

11. The method as set forth in claim 6, wherein:
the silicon oxide-binding tag contains a polypeptide; and
not less than 5/14 and not more than 4/7 of all amino acids constituting the polypeptide are arginine.

12. The silicon oxide-binding tag as set forth in claim 9, wherein not less than 3/7 and not more than 4/7 of all amino acids constituting the polypeptide are arginine.

13. The kit as set forth in claim 10, wherein:
the silicon oxide-binding tag contains a polypeptide; and
not less than 5/14 and not more than 4/7 of all amino acids constituting the polypeptide are arginine.

* * * * *